US009372193B2

(12) United States Patent
Von Hoff et al.

(10) Patent No.: US 9,372,193 B2
(45) Date of Patent: Jun. 21, 2016

(54) SYSTEM AND METHOD FOR DETERMINING INDIVIDUALIZED MEDICAL INTERVENTION FOR A DISEASE STATE

(71) Applicant: Caris MPI, Inc., Irving, TX (US)

(72) Inventors: Daniel D. Von Hoff, Scottsdale, AZ (US); Robert J. Penny, Lebanon, IN (US)

(73) Assignee: Caris MPI, Inc., Irving, TX (US)

( * ) Notice: Subject to any disclaimer, the term of this patent is extended or adjusted under 35 U.S.C. 154(b) by 0 days.

(21) Appl. No.: 14/473,881

(22) Filed: Aug. 29, 2014

(65) Prior Publication Data

US 2014/0371111 A1 Dec. 18, 2014

Related U.S. Application Data

(63) Continuation of application No. 14/143,959, filed on Dec. 30, 2013, now Pat. No. 8,914,239, which is a continuation of application No. 11/750,721, filed on May 18, 2007, now Pat. No. 8,700,335.

(60) Provisional application No. 60/747,645, filed on May 18, 2006.

(51) Int. Cl.

| G01N 33/48 | (2006.01) |
|---|---|
| G01N 33/574 | (2006.01) |
| G06F 19/00 | (2011.01) |
| C12Q 1/68 | (2006.01) |
| G06F 19/20 | (2011.01) |
| G01N 33/68 | (2006.01) |
| G06F 19/18 | (2011.01) |
| G06F 19/28 | (2011.01) |

(52) U.S. Cl.
CPC ........ *G01N 33/57488* (2013.01); *C12Q 1/6883* (2013.01); *C12Q 1/6886* (2013.01); *G01N 33/574* (2013.01); *G01N 33/6893* (2013.01); *G06F 19/18* (2013.01); *G06F 19/20* (2013.01); *G06F 19/34* (2013.01); *G06F 19/345* (2013.01); *G06F 19/3481* (2013.01); *G06F 19/3487* (2013.01); *C12Q 2600/106* (2013.01); *C12Q 2600/158* (2013.01); *G01N 2333/71* (2013.01); *G01N 2333/914* (2013.01); *G01N 2333/91205* (2013.01); *G06F 19/28* (2013.01)

(58) Field of Classification Search
CPC ....................................................... G06F 19/34
USPC ........................................................... 702/19
See application file for complete search history.

(56) References Cited

U.S. PATENT DOCUMENTS

| 5,942,385 | A | 8/1999 | Hirth |
|---|---|---|---|
| 6,143,737 | A | 11/2000 | Clarke et al. |
| 6,498,144 | B1 | 12/2002 | Goldberg et al. |
| 8,831,890 | B2 | 9/2014 | Von Hoff et al. |
| 8,880,350 | B2 | 11/2014 | Von Hoff et al. |
| 8,914,239 | B2 | 12/2014 | Von Hoff et al. |
| 9,053,224 | B2 | 6/2015 | Von Hoff et al. |
| 9,058,418 | B2 | 6/2015 | Von Hoff et al. |
| 9,064,045 | B2 | 6/2015 | Von Hoff et al. |
| 9,092,392 | B2 | 7/2015 | Von Hoff et al. |
| 2003/0086934 | A1 | 5/2003 | Botstein et al. |
| 2004/0235020 | A1 | 11/2004 | Burczynski et al. |
| 2005/0026194 | A1 | 2/2005 | Mu |
| 2005/0181377 | A1 | 8/2005 | Markovic |
| 2005/0222163 | A1 | 10/2005 | Eck et al. |
| 2005/0244880 | A1 | 11/2005 | Kallioniemi |
| 2005/0256745 | A1 | 11/2005 | Dalton |
| 2006/0008807 | A1 | 1/2006 | O'Hara et al. |
| 2006/0019256 | A1* | 1/2006 | Clarke et al. ............ 435/6 |
| 2007/0161008 | A1 | 7/2007 | Morrison et al. |
| 2007/0172844 | A1* | 7/2007 | Lancaster et al. ........ 435/6 |
| 2007/0231797 | A1 | 10/2007 | Fan et al. |
| 2008/0090232 | A1 | 4/2008 | Engelhard |
| 2008/0118576 | A1 | 5/2008 | Theodorescu et al. |
| 2009/0208935 | A1 | 8/2009 | Roninson et al. |
| 2009/0291434 | A1 | 11/2009 | Cowens et al. |
| 2011/0015259 | A1 | 1/2011 | Ring et al. |
| 2011/0118298 | A1 | 5/2011 | Fritz et al. |
| 2011/0230360 | A1 | 9/2011 | Stephan et al. |
| 2013/0287772 | A1 | 10/2013 | Halbert et al. |

FOREIGN PATENT DOCUMENTS

| WO | WO 99/66024 A1 | 12/1999 |
|---|---|---|
| WO | WO 00/70085 A2 | 11/2000 |

OTHER PUBLICATIONS

Advisory Action dated Jan. 29, 2015 for U.S. Appl. No. 14/187,020.
Advisory Action dated Jan. 29, 2015 for U.S. Appl. No. 14/187,028.
Ciardiello et al. A novel approach in the treatment of cancer: targeting the epidermal growth factor receptor. Clin Cancer Res. 2001; 7: 2958-70.
Debiec-Rychter et al. Use of c-KIT/PDGFRA mutational analysis to predict the clinical response to imatinib in patients with advanced gastrointestinal stromal tumours entered on phase I and II studies of the EORTC soft tissue and bone sarcoma group. European Journal of Cancer. 2004; 40(5): 689-695.

(Continued)

*Primary Examiner* — Jerry Lin
(74) *Attorney, Agent, or Firm* — Ramin Akhavan

(57) ABSTRACT

A system and method for determining individualized medical intervention for a particular disease state, and especially for cancers, that includes the molecular profiling of a biological sample from the patient, determining whether any molecular findings including one or more genes, one or more gene expressed proteins, one or more molecular mechanisms, and/or combinations of such exhibit a change in expression compared to a reference, and identifying a non-specific disease therapy or agent capable of interacting with the genes, gene expressed proteins, molecular mechanisms, or combinations of such molecular findings that exhibited a change in expression.

14 Claims, 28 Drawing Sheets

(56) References Cited

OTHER PUBLICATIONS

Di Lorenzo et al. Expression of epidermal growth factor receptor correlates with disease relapse and progression to androgen-independence in human prostate cancer. Clin Cancer Res. 2002; 8: 3438-44.
Holzbeierlein et al. Gene expression analysis of human prostate carcinoma during hormonal therapy identifies androgen-responsive genes and mechanisms of therapy resistance. An J Path. 2004; 164: 217-27.
Latil et al. Evaluation of androgen, estrogen (ERa and ER/β), and progesterone receptor expression in human prostate cancer by real-time quantitative reverse transcription-polymerase chain reaction assays. Cancer Res. 2001; 61: 1919-26.
Madaan et al. Cytoplasmic induction and over-expression of cyclooxygenase-2 in human prostate cancer: implications for prevention and treatment. BJU Int. 2000; 86: 736-41.
Lievre et al. KRAS mutation status is predictive of response to cetuximab therapy in colorectal cancer. Cancer Research. 2006; 66(8): 3992-3995.
Lukashova-V.Zangen. Ependymoma gene expression profiles associated with histological subtype, proliferation, and patient survival. Acta Neuropathol. 2007; 113: 325-337.
Notice of Allowance dated Sep. 23, 2014 for U.S. Appl. No. 14/170,466, now issued as U.S. Pat. No. 8,880,350.
Notice of Allowance dated Oct. 27, 2014 for U.S. Appl. No. 14/143,959, now issued as U.S. Pat. No. 8,914,239.
Notice of Allowance dated Jan. 29, 2015 for Chinese application No. 201080016438.9 (translation at p. 1).
Notice of Allowance dated Mar. 13, 2015 for U.S. Appl. No. 14/175,800, now issued as U.S. Pat. No. 9,064,045.
Notice of Allowance dated Mar. 17, 2015 for U.S. Appl. No. 14/187,008, now issued as U.S. Pat. No. 9,058,418.
Notice of Allowance dated Mar. 26, 2015 for U.S. Appl. No. 14/175,728, now issued as U.S. Pat. No. 9,053,224.
Notice of Allowance dated May 21, 2015 for U.S. Appl. No. 14/175,781, now issued as U.S. Pat. No. 9,092,392.
Office Action dated Aug. 26, 2014 for Chinese application No. 201080016438.9 (translation at pp. 13-23).
Office Action dated Sep. 24, 2014 for U.S. Appl. No. 14/175,800.
Office Action dated Oct. 9, 2014 for Canadian application No. 2,651,995.
Office Action dated Oct. 10, 2014 for Chinese application No. 201310356643.5 (translation at pp. 8-14).
Office Action dated Oct. 21, 2014 for U.S. Appl. No. 14/175,781.
Office Action dated Oct. 23, 2014 for U.S. Appl. No. 14/170,450.
Office Action dated Oct. 24, 2014 for U.S. Appl. No. 14/187,008.
Office Action dated Oct. 27, 2014 for U.S. Appl. No. 14/175,728.
Office Action dated Nov. 5, 2014 for U.S. Appl. No. 14/170,370.
Office Action dated Nov. 12, 2014 for U.S. Appl. No. 14/187,028.
Office Action dated Nov. 13, 2014 for U.S. Appl. No. 14/187,020.
Office Action dated Nov. 15, 2014 for Chinese application No. 200980148416.5 (translation at pp. 8-10).
Office Action dated Nov. 19, 2014 for Israeli application No. 195266 (translation at pp. 4-9).
Office Action dated Dec. 14, 2014 for Israeli application No. 214400 (translation at pp. 2-3).
Office Action dated Mar. 4, 2015 for Australian application No. 2014200048.
Office Action dated May 7, 2015 for U.S. Appl. No. 14/473,871.
Office Action dated May 21, 2015 for Chinese application No. 201310356643.5 (translation not yet available).
Office Action dated Jun. 10, 2015 for U.S. Appl. No. 13/188,350.
Office Action dated Jun. 16, 2015 for U.S. Appl. No. 14/187,015.
Office Action dated Jun. 18, 2015 for U.S. Appl. No. 14/249,261.
Paronetto et al. Expression of a truncated form of the c-kit tyrosine kinase receptor and activation of src kinase in human prostatic cancer. AJP. 2004; 164: 1243-51.
Press Release "Personalized Medicine Helps Cancer Patients Survive," EurekAlert, published online Apr. 19, 2009.
Smith, "AACR: 'Molecular Profile' Improves Outcome in Advanced Cancer" Medpage Today, published online Apr. 24, 2009.
Takei et al. Isolation of a novel TP53 target gene from a colon cancer cell line carrying a highly regulated wild-type TP53 expression system. Genes Chromosomes Cancer. 1998; 23(1):1-9 (abstract).
Tomasini et al. TP53INP1s and homeodomain-interacting protein kinase-2 (HIPK2) are partners in regulating p53 activity. J Biol Chem. 2003; 278:37722-29.
Bandyopadhyay et al. The tumor metastasis suppressor gene Drg-1 downregulates the expression of activating transcription factor 3 in prostate cancer. Cancer Research. 2006; 66: 11983-11990.
De Roock et al. KRAS, BRAF, PIK3CA, and PTEN mutations: implications for targeted therapies in metastatic colorectal cancer. The Lancet Oncology. 2011; 12: 594-603.
Gautam et al. RRM1-induced metastasis suppression through PTEN-regulated pathways. Oncogene. 2003; 22: 2135-2142.
Lurkin et al. Two multiplex assays that simultaneously identify 22 possible mutation sites in the KRAS, BRAF, NRAS and PIK3CA genes. PLoS ONE. 2010; 5(1): e8802.
Notice of Allowance dated Jul. 15, 2014 for U.S. Appl. No. 14/052,503, now issued as U.S. Pat. No. 8,831,890.
Notice of Allowance dated Dec. 9, 2015 for U.S. Appl. No. 14/187,015.
Office Action dated Apr. 23, 2014 for Israeli application No. 214400 (English translation only).
Office Action dated Jun. 17, 2014 for U.S. Appl. No. 14/143,959.
Office Action dated Jul. 23, 2014 for U.S. Appl. No. 14/170,450.
Office Action dated Jul. 29, 2014 for U.S. Appl. No. 14/150,624.
Office Action dated Jul. 29, 2014 for U.S. Appl. No. 14/170,466.
Office Action dated Aug. 4, 2014 for U.S. Appl. No. 14/187,028.
Office Action dated Aug. 12, 2014 for U.S. Appl. No. 14/187,020.
Office Action dated Sep. 1, 2015 for U.S. Appl. No. 14/551,345.
Office Action dated Sep. 3, 2015 for U.S. Appl. No. 14/473,871.
Office Action dated Sep. 21, 2015 for U.S. Appl. No. 14/551,364.
Office Action dated Nov. 27, 2015 for U.S. Appl. No. 14/187,028.
Randall-Whitis et al. cDNA microarray analysis of gene expression in ovarian cancer cells after treatment with carboplatin and paclitaxel. Cancer Genomics & Proteomics. 2006; 3: 289-294.
Zhu et al., Role of KRAS and EGFR as Biomarkers of Response to Erlotinib in National Cancer Institute of Canada Clinical Trials Group Study BR.21. J Clin Oncol. 2008; 26:4268-4275.

* cited by examiner

| MOLECULAR PROFILING INSTITUTE | PATIENT INFORMATION<br>NAME: SAMPLE PATIENT<br>SEX: FEMALE<br>DOB: 6/1/1974<br>SSN#: 123-45-6789 | PHYSICIAN INFORMATION<br>SOME DOCTOR, M.D.<br>1234 E. SOUTH ST.<br>TUCSON, AX 12345<br>480-123-4567 |
|---|---|---|
| | REPORT INFORMATION | VER 1.6.2:4-25-06 |
| | DATE SPECIMEN RECEIVED: 02/01/2006 DATE REPORTED: 02/09/2006 CASE NO. MP-TN06-05040<br>DATE SPECIMEN COLLECTED AT HOST MEDICAL CENTER: 01/24/2006 | |

| SPECIAL STUDIES |
|---|
| RESULTS AND INTERPRETATION |

INTERPRETATION:

REVIEW OF PATHOLOGY SLIDES: (RECEIVED FROM MAIN HOSPITAL, TUCSON, AZ, ONE PARAFFIN BLOCK LABELED M01-123 AND FROZEN TISSUE).

PELVIC AND RETROPERITONEAL TUMOR: INFLAMMATORY MYOFIBROLASTIC TUMOR.

POSSIBLE AGENTS THAT MIGHT INTERACT WITH CANDIDATE GENE TARGETS:

| ASSAY* | CANDIDATE TARGET | SIGNIFICANT RESULT | POSSIBLE AGENT(S) |
|---|---|---|---|
| MICROARRAY | NFKBIA | (INCREASED 1.78)** | VELCADE |
| IHC | C-KIT | (INCREASED +2, 90%) | GLEEVEC, SUTENT |
| MICROARRAY | PDGFRA | (INCREASED 4.74)** | GLEEVEC, SORAFENIB, SUTENT |
| MICROARRAY | GART | (INCREASED 1.90)** | ALIMTA |
| MICROARRAY | VDR | (INCREASED 37.30)** | CALCITRIOL |
| MICROARRAY | ADA | (INCREASED 5.26)** | PENTOSTATIN |
| MICROARRAY | TOP1 | (INCREASED 2.78)** | TOPOTECAN, CAMPTOSAR (CPT11) |
| MICROARRAY | HIF1A | (INCREASED 4.03)** | AVASTIN, SORAFENIB, SUTENT |
| MICROARRAY | DNMT1 | (INCREASED 1.51)** | VIDAZA (5-AZACYTIDINE) |

*IHC = IMMUNOHISTOCHEMISTRY
** INCREASED OR DECREASED ARE RELATIVE TO NORMAL CONTRLS.

FIG.3A

| MOLECULAR PROFILING INSTITUTE | PATIENT INFORMATION | PHYSICIAN INFORMATION |
|---|---|---|
| | NAME: SAMPLE PATIENT<br>SEX: FEMALE<br>DOB: 6/1/1974<br>SSN#: 123-45-6789 | SOME DOCTOR, M.D.<br>1234 E. SOUTH ST.<br>TUCSON, AX 12345<br>480-123-4567 |
| | REPORT INFORMATION  VER 1.6.2:4-25-06 | |
| | DATE SPECIMEN RECEIVED: 02/01/2006  DATE REPORTED: 02/09/2006  CASE NO. MP-TN06-05040<br>DATE SPECIMEN COLLECTED AT HOST MEDICAL CENTER: 01/24/2006 | |

SPECIAL STUDIES
RESULTS AND INTERPRETATION

ADVANCED IMMUNOHISTOCHEMICAL ANALYSIS:

| GENE EXPRESSED PROTEIN | CONCLUSION | SPECIFICITY | INTENSITY | % | TARGET STATUS* |
|---|---|---|---|---|---|
| HER2/NEU | NEGATIVE | | | | |
| ER | NEGATIVE | | | | |
| PR | NEGATIVE | | | | |
| C-KIT | POSITIVE | SPECIFIC | 2 | 90 | TARGET |
| EGFR | NEGATIVE | | | | |
| COX-2 | NEGATIVE | | | | |
| ANDROGEN RECEPTOR | NEGATIVE | | | | |
| CD52 | NEGATIVE | | | | |
| PDGFR | NEGATIVE | NON-SPECIFIC | | | |
| CD25 | NEGATIVE | | | | |

* 2+ IHC IN GREATER THAN 30% OF THE TUMOR CELLS HAS BEEN CHOSEN AS A CONSERVATIVE DIVIDING POINT TO REPORT A POTENTIAL TARGET AS POSITIVE TO HELP INCREASE PHARMACOLOGIC EFFECTIVENESS.

IMMUNOHISTOCHEMICAL TESTS NOT PERFORMED

| | | |
|---|---|---|
| IL-2 | TOPOISOMERASE I | MLH1 |
| NF-KAPPA BETA | TOPOISOMERASE II | MSH2 |
| THYMIDYLATE SYNTHASE | RETINOIC ACID RECEPTOR | CD20 |
| ERCC3 (HELICASE) | RXR | P53 |
| THYMIDINE PHOSPHORYLASE | ORNITHINE DECARBOXYLASE | CYCLIN D1 |
| NGF | SOMATOSTATIN | BCL-2 |
| MTAP | RAS (MUTATED) | VEGF |
| MAP KINASE PROTEIN | ASPARAGINE SYNTHETASE | |
| XANTHINE OXIDASE | | |

FIG.3B

| MOLECULAR PROFILING INSTITUTE | PATIENT INFORMATION | PHYSICIAN INFORMATION |
|---|---|---|
| | NAME: SAMPLE PATIENT<br>SEX: FEMALE<br>DOB: 6/1/1974<br>SSN#: 123-45-6789 | SOME DOCTOR, M.D.<br>1234 E. SOUTH ST.<br>TUCSON, AX 12345<br>480-123-4567 |
| | REPORT INFORMATION | VER 1.6.2:4-25-06 |
| | DATE SPECIMEN RECEIVED: 02/01/2006  DATE REPORTED: 02/09/2006  CASE NO. MP-TN06-05040<br>DATE SPECIMEN COLLECTED AT HOST MEDICAL CENTER: 01/24/2006 | |

SPECIAL STUDIES
MICROARRAY RESULTS

MICROARRAY ANALYSIS:

| GENE | RATIO | EXPRESSION* | ANALYSIS | GENE | RATIO | EXPRESSION* | ANALYSIS | GENE | RATIO | EXPRESSION* | ANALYSIS |
|---|---|---|---|---|---|---|---|---|---|---|---|
| AR | 0.02 | UNDER EXPRESSED | | EGFR | 1.16 | NO CHANGE | | ZAP70 | 3.00 | NO CHANGE | |
| ESR1 | 0.09 | UNDER EXPRESSED | | OGFR | 1.17 | NO CHANGE | | ZAP70 | 3.02 | NO CHANGE | |
| PGR | 0.10 | UNDER EXPRESSED | | MLH1 | 1.19 | NO CHANGE | | CD33 | 3.05 | OVER EXPRESSED | |
| VEGF | 0.33 | UNDER EXPRESSED | | VHL | 1.22 | NO CHANGE | | ZAP70 | 3.06 | NO CHANGE | |
| KIT | 0.51 | UNDER EXPRESSED | | TNF | 1.29 | NO CHANGE | | ZAP70 | 3.13 | NO CHANGE | |
| PDGFC | 0.53 | UNDER EXPRESSED | | RARA | 1.38 | NO CHANGE | | ZAP70 | 3.18 | NO CHANGE | |
| RXRB | 0.62 | NO CHANGE | | HSPCA | 1.42 | NO CHANGE | | ZAP70 | 3.40 | NO CHANGE | |
| TOP2B | 0.62 | UNDER EXPRESSED | | TXNRD1 | 1.42 | NO CHANGE | | CD33 | 3.52 | OVER EXPRESSED | |
| RAF1 | 0.68 | NO CHANGE | | ASNS | 1.44 | NO CHANGE | | HIF1A | 3.84 | OVER EXPRESSED | |
| ERBB2 | 0.69 | NO CHANGE | | DNMT1 | 1.51 | OVER EXPRESSED | | HIF1A | 3.85 | OVER EXPRESSED | |
| ERCC3 | 0.71 | NO CHANGE | | NFKB2 | 1.74 | NO CHANGE | | HIF1A | 3.88 | OVER EXPRESSED | |
| BCL2 | 0.71 | NO CHANGE | | NFKBIA | 1.78 | OVER EXPRESSED | | HIF1A | 3.90 | OVER EXPRESSED | |
| PDGFRB | 0.78 | NO CHANGE | | PTGS2 | 1.81 | NO CHANGE | | HIF1A | 3.90 | OVER EXPRESSED | |
| BCL2 | 0.80 | NO CHANGE | | BRCA2 | 1.83 | NO CHANGE | | HIF1A | 3.91 | OVER EXPRESSED | |
| GSTP1 | 0.85 | NO CHANGE | | GART | 1.90 | OVER EXPRESSED | | HIF1A | 3.94 | OVER EXPRESSED | |
| SPARC | 0.92 | NO CHANGE | | CDW52 | 2.15 | OVER EXPRESSED | | HIF1A | 3.97 | OVER EXPRESSED | |
| HDAC1 | 0.95 | NO CHANGE | | ZAP70 | 2.18 | NO CHANGE | | HIF1A | 4.01 | OVER EXPRESSED | |
| POLA | 0.98 | NO CHANGE | | FOLR2 | 2.21 | OVER EXPRESSED | | HIF1A | 4.03 | OVER EXPRESSED | |
| MSH2 | 0.98 | NO CHANGE | | ZAP70 | 2.76 | NO CHANGE | | PDGFRA | 4.74 | OVER EXPRESSED | |
| CES2 | 1.05 | NO CHANGE | | TOP1 | 2.78 | OVER EXPRESSED | | TK1 | 4.94 | OVER EXPRESSED | |
| VEGF | 1.09 | NO CHANGE | | MS4A1 | 2.86 | NO CHANGE | | IL2RA | 5.07 | NO CHANGE | |
| SSTR1 | 1.11 | NO CHANGE | | ZAP70 | 2.86 | NO CHANGE | | ADA | 5.26 | OVER EXPRESSED | |
| PTEN | 1.11 | NO CHANGE | | ZAP70 | 2.92 | NO CHANGE | | TOP2A | 9.34 | NO CHANGE | |
| | | | | | | | | TYMS | 22.95 | OVER EXPRESSED | |
| | | | | | | | | VDR | 37.30 | OVER EXPRESSED | |

*"NO CHANGE" INDICATES THAT THERE IS NO DIFFERENCE IN EXPRESSION FOR THIS GENE BETWEEN THE TUMOR AND CONTROL TISSUES AT A SIGNIFICANCE LEVEL OF P<=0.001. A SIGNIFICANCE LEVEL OF P<=0.001 HAS BEEN CHOSEN SINCE GENES PASSING THIS THRESHOLD CAN BE VALIDATED AS DIFFERENTIALLY EXPRESSED BY ALTERNATIVE METHODS APPROXIMATELY 95% OF THE TIME.

FIG.3C

PATIENT: SAMPLE PATIENT    CASE NO. MP-TN06-05040    DATE REPORTED: 2/9/2006

| CLINICAL INFORMATION |
|---|

CLINICAL HISTORY

THE PATIENT WAS DIAGNOSED WITH INFLAMATORY MYOFIBROBLASTIC TUMOR IN FEB, 2004. AT THAT TIME A LARGE MASS WAS REMOVED FROM HER ABDOMEN. THE PATIENT NOW HAS RECURRENT MASSES ON HER LEFT UPPER QUADRANT AND IN THE PELVIS. PER THE PATIENT CHART, DR SOME REVIEWED THIS CASE WITH DR VON HOFF AND IT WAS AGREED THAT PERFORMING DNA MICROARRAY AND IHC TESTING ON THIS PATIENT MAY PROVIDE INSIGHT INTO FURTHER TREATMENT OPTIONS.

SPECIMENS SUBMITTED

RECEIVED FROM MAIN HOSPITAL, TUCSON, AZ, ONE PARAFFIN BLOCK LABELED M01-123 AND FROZEN TISSUE WITH THE ACCOMPANYING SURGICAL PATHOLOGY REPORT.

DISCLAIMER

THESE TESTS WERE DEVELOPED BY MOLECULAR PROFILING AND THEIR PERFORMANCE CHARACTERISTICS DETERMINED BY MOLECULAR PROFILING. IT HAS NOT BEEN CLEARED OR APPROVED BY THE U.S. FOOD AND DRUG ADMINISTRATION (FDA). THESE TESTS ARE PERMITTED FOR CLINICAL PURPOSES AND SHOULD NOT BE REGARDED AS PURELY INVESTIGATIONAL OR FOR RESEARCH. MOLECULAR PROFILING IS CERTIFIED UNDER THE CLINICAL LABORATORY IMPROVEMENT AMENDMENTS OF 1988 (CLIA) AS QUALIFIED TO PERFORM HIGH-COMPLEXITY CLINICAL TESTING.

DECISIONS REGARDING CARE AND TREATMENT SHOULD NOT BE BASED ON A SINGLE TEST SUCH AS THIS TEST. RATHER DECISIONS ON CARE AND TREATMENT SHOULD BE BASED ON THE INDEPENDENT MEDICAL JUDGMENT OF THE TREATING PHYSICIAN TAKING INTO CONSIDERATION ALL AVAILABLE INFORMATION CONCERNING THE PATIENT'S CONDITION, INCLUDING OTHER LABORATORY TESTS, IN ACCORDANCE WITH THE STANDARD OF CARE IN A GIVEN COMMUNITY.

THE FINDING OF A TARGET DOES NOT NECESSARILY INDICATE PHARMACOLOGIC EFFECTIVENESS.

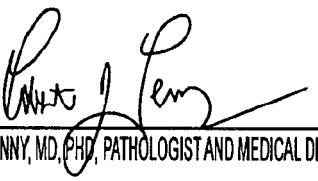

ROBERT J. PENNY, MD, PHD, PATHOLOGIST AND MEDICAL DIRECTOR    DATE 2/9/2006

SYSTEM AND METHOD FOR DETERMINING INDIVIDUALIZED MEDICAL INTERVENTION FOR A DISEASE STATE

RELATED APPLICATIONS

This application is a continuation of U.S. patent application Ser. No. 14/143,959, filed on Dec. 30, 2013, now U.S. Pat. No. 8,914,239 which issued on Dec. 16, 2014, which is a continuation of U.S. patent application Ser. No. 11/750,721, filed on May 18, 2007, now U.S. Pat. No. 8,700,335 which issued on Apr. 15, 2014, which claims the benefit of U.S. Provisional Patent Application No. 60/747,645, filed May 18, 2006, each of which applications is incorporated herein by reference in its entirety.

FIELD OF INVENTION

The present invention generally relates to the application of molecular profiling to provide a system and method for determining medical intervention for a particular disease state. The system and method can be conducted at any stage of the disease. In particular, the present invention relates to a system and method for determining medical intervention for a seriously diseased patient, for example, a patient with cancer that has progressed on at least two chemotherapeutic or hormonal regimens, where the method includes the molecular profiling of a biological sample from the patient, determining whether any molecular findings including one or more genes, gene expressed proteins, molecular mechanisms, and/or combinations of such molecular findings exhibit a change in expression compared to a normal reference, and identifying a drug therapy capable of interacting with the genes, gene expressed proteins, molecular mechanisms, or combinations of such molecular findings that exhibited a change in expression.

BACKGROUND

Disease states in patients are typically treated with treatment regimens or therapies that are selected based on clinical based criteria; that is, a treatment therapy or regimen is selected for a patient based on the determination that the patient has been diagnosed with a particular disease (which diagnosis has been made from classical diagnostic assays). Although the molecular mechanisms behind various disease states have been the subject of studies for years, the specific application of a diseased individual's molecular profile in determining treatment regimens and therapies for that individual has been disease specific and not widely pursued.

Some treatment regimens have been determined using molecular profiling in combination with clinical characterization of a patient such as observations made by a physician (such as a code from the International Classification of Diseases, for example, and the dates such codes were determined), laboratory test results, x-rays, biopsy results, statements made by the patient, and any other medical information typically relied upon by a physician to make a diagnosis in a specific disease. However, using a combination of selection material based on molecular profiling and clinical characterizations (such as the diagnosis of a particular type of cancer) to determine a treatment regimen or therapy presents a risk that an effective treatment regimen may be overlooked for a particular individual since some treatment regimens may work well for different disease states even though they are associated with treating a particular type of disease state.

Patients with metastatic cancer are of particular concern for treating physicians. The majority of patients with metastatic cancer eventually run out of treatment options for their tumors. These patients have very limited options after their tumor has progressed on standard front line and second line (and sometimes third line and beyond) therapies. Although these patients may participate in Phase I and Phase II clinical trials for new anticancer agents, they must usually meet very strict eligibility criteria to do so. Studies have shown that when patients participate in these types of trials, the new anticancer agent may give response rates of anywhere from 5% to 10% on average in Phase I settings to 12% in Phase II settings. These patients also have the option of electing to receive the best supportive care to treat their symptoms.

There has recently been an explosion of interest in developing new anticancer agents that are more targeted against a cell surface receptor or an up regulated or amplified gene product. This approach has met with some success (e.g. Herceptin against HER2/neu in breast cancer cells, rituximab against CD20 in lymphoma cells, bevacizamab against VEGF, Cetuximab against EGFR, etc.). However, patients' tumors still eventually progress on these therapies. If a larger number of targets or molecular findings such as molecular mechanisms, genes, gene expressed proteins, and/or combinations of such were measured in a patient's tumor, one may find additional targets or molecular findings that can be exploited by using specific therapeutic agents. Identifying multiple agents that can treat multiple targets or underlying mechanisms would provide a metastatic cancer patient with a viable therapeutic alternative to those treatment regimens which currently exist.

Accordingly, there is a need for a system and method for determining an individualized medical intervention for a disease state based on molecular profiling that is used to target specific genes and/or gene expressed proteins with specific drugs or agents that is independent of disease lineage diagnosis.

SUMMARY

The present invention is directed to a system and method for determining individualized medical intervention for a particular disease state. One exemplary method of the present invention for determining medical intervention for a disease state includes the steps of performing a test for a gene and/or a test for a gene expressed protein from a biological sample of a diseased individual, determining which genes and/or gene expressed proteins exhibited change in expression compared to a reference, and identifying a drug therapy used to interact with the gene and/or gene expressed proteins that exhibited a change of expression that is not single disease restricted. In one aspect of this exemplary embodiment of the invention, the step of identifying a drug therapy used to interact with a gene and/or gene expressed protein that exhibited a change in expression may include the step of identifying a drug therapy from an automated review of an extensive literature database and/or data generated from clinical trials.

In another aspect of the above-described exemplary embodiment of the present invention, the step of performing a test for a gene and/or a test for a gene expressed protein may include the step of performing an immunohistochemical (IHC) analysis and/or a micro array analysis. Further, the step of performing a micro array analysis may include the step of performing an analysis using an expression micro array, a comparative genomic hybridization (CGH) micro array, a single nucleotide polymorphism (SNP) micro array, a fluorescent in-situ hybridization (ISH), an in-situ hybridization (ISH), and a proteomic array. In addition, the step of performing an IHC analysis may include the step of performing an IHC analysis for a gene expressed protein which includes at least one of Her2/Neu, ER, PR, c-kit, EGFR, MLH1, MSH2, CD20, p53, Cyclin D1, bcl2, COX-2, Androgen receptor, CD52, PDGFR, AR, CD25, and VEGF.

In another aspect of the invention, the step of performing a micro array analysis in the above-described exemplary method for determining medical intervention for a disease state may include the step of performing a micro array analysis for a gene which includes at least one of BCL2, HIF1A, AR, ESR1, PDGFRA, KIT, PDGFRB, CDW52, ZAP70, PGR, SPARC, GART, GSTP1, NFKBIA, MSH2, TXNRD1, HDAC1, PDGFC, PTEN, CD33, TYMS, RXRB, ADA, TNF, ERCC3, RAF1, VEGF, TOP1, TOP2A, BRCA2, TK1, FOLR2, TOP2B, MLH1, IL2RA, DNMT1, HSPCA, ERBR2, ERBB2, SSTR1, VHL, VDR, PTGS2, POLA, CES2, EGFR, OGFR, ASNS, NFKB2, RARA, MS4A1, DCK, DNMT3A, EREG, Epiregulin, FOLR1, GNRH1, GNRHR1, FSHB, FSHR, FSHPRH1, folate receptor, HGF, HIG1, IL13RA1, LTB, ODC1, PPARG, PPARGC1, Lymphotoxin Beta Receptor, Myc, Topoisomerase II, TOPO2B, TXN, VEGFC, ACE2, ADH1C, ADH4, AGT, AREG, CA2, CDK2, caveolin, and NFKB1.

In yet another aspect of the above-described exemplary method of the present invention, the step of performing a test for a gene and/or a test for a gene expressed protein from a biological sample of a diseased individual may include the step of performing an immunohistochemical analysis on a tumor and the step of determining which genes and/or gene expressed proteins exhibit a change in expression compared to a reference may include the step of determining whether 30% or more of the tumor cells were +2 or greater standing for a particular gene expressed protein. In still another aspect of the above-described exemplary method of the present invention, the step of performing a test for a gene and/or a test for a gene expressed protein from a biological sample of a diseased individual may include the step of performing a micro array analysis on a tumor and the step of determining which genes and/or gene expressed proteins exhibit a change in expression compared to a reference may include the step of identifying which genes are up-regulated or down-regulated by determining whether the full change of expression for a particular gene relative to a normal tissue of origin reference is significant at p<0.001. Furthermore, the above-described exemplary method of the present invention for determining medical intervention for a disease state may also include the step of providing a patient profile report which identifies the change in expression for the genes and/or gene expressed proteins along with a possible drug therapy for interaction with each of the genes and/or gene expressed proteins that exhibit a change in expression.

Another exemplary embodiment of the present invention is directed to a method for identifying a drug therapy capable of interacting with a molecular target which includes the steps of identifying a molecular target in a plurality of diseased individuals that exhibits a change in expression when compared to a normal reference, administrating a drug therapy to the diseased individuals that exhibit the change in expression of the molecular target, and determining any changes in the molecular target of the diseased individuals after the drug therapy. Further, in one aspect of this exemplary embodiment of a method for identifying a drug therapy capable of interacting with the molecular target, the step of identifying a molecular target in a plurality of diseased individuals that exhibits a change in expression when compared to a normal reference may include the step of performing a test for a gene and/or a test for a gene expressed protein from a biological sample of the diseased individual where the test comprises an immunohistochemical (IHC) analysis and/or a micro array analysis.

In yet another exemplary embodiment of the present invention, a system is provided for determining individualized medical intervention for a disease state where the system includes a host server, a user interface for accessing the host server to access and input data, a processor for processing the inputted data, a memory coupled to the processor for storing the processed data and instructions for: a) accessing a molecular profile taken from a biological specimen of a patient b) determining whether at least one of a gene, a gene expressed protein, a molecular mechanism, and other molecular findings resulting from the molecular profile exhibit change in expression compared to a normal reference, and c) accessing a drug therapy database to identify one or more drug therapies that interact with a gene, a gene expressed protein, a molecular mechanism, and/or other molecular findings that exhibited a change in expression, and a display means for displaying a gene, a gene expressed protein, a molecular mechanism, and other molecular findings exhibiting a change in expression and the drug therapies that interact with them. With respect to the exemplary embodiment of the present invention directed to the system for determining individualized medical intervention for a disease state, the molecular profile taken from the biological specimen may include the same immunohistochemical (IHC) analysis and micro array analysis described above with reference to the first exemplary embodiment of the present invention. In addition, the different types of these analyses along with the genes analyzed using these analyses may be the same as those described above with reference to the first exemplary embodiment of the present invention which is directed to a method for determining medical intervention for a disease state.

Still another exemplary embodiment of the present invention is directed to a method for determining medical intervention for a disease state which includes the steps of performing at least one molecular test for at least one target from a biological sample of a diseased individual, determining whether the target exhibits a change in expression compared to a reference, and identifying at least one non-disease specific agent that interacts with the target that exhibits a change in expression. The step of identifying at least one non-disease specific agent that interacts with the target may include the step of identifying a drug therapy from an automated review of an extensive literature base and/or an automated review of data generated from clinical trials. In addition, the exemplary embodiment of the present invention directed to a method for determining medical intervention for a disease state may also include the step of providing a patient profile report which includes the patient's test results for various targets and any proposed therapies based on those results.

The step of performing at least one molecular test for at least one target from a biological sample of a diseased individual in the exemplary embodiment of the present invention directed to a method for determining medical intervention for a disease state may include all of the above-described analyses relating to immunohistochemical (IHC) analysis and micro array analysis and the genes analyzed using those analyses.

BRIEF DESCRIPTION OF THE DRAWINGS

FIGS. 3A through 3D illustrate an exemplary patient profile report in accordance with step 80 of FIG. 2.

FIGS. 15-25 are computer screen print outs associated with various parts of the information-based personalized medicine drug discovery system and method shown in FIGS. 5-14.

DETAILED DESCRIPTION

Figure 1:
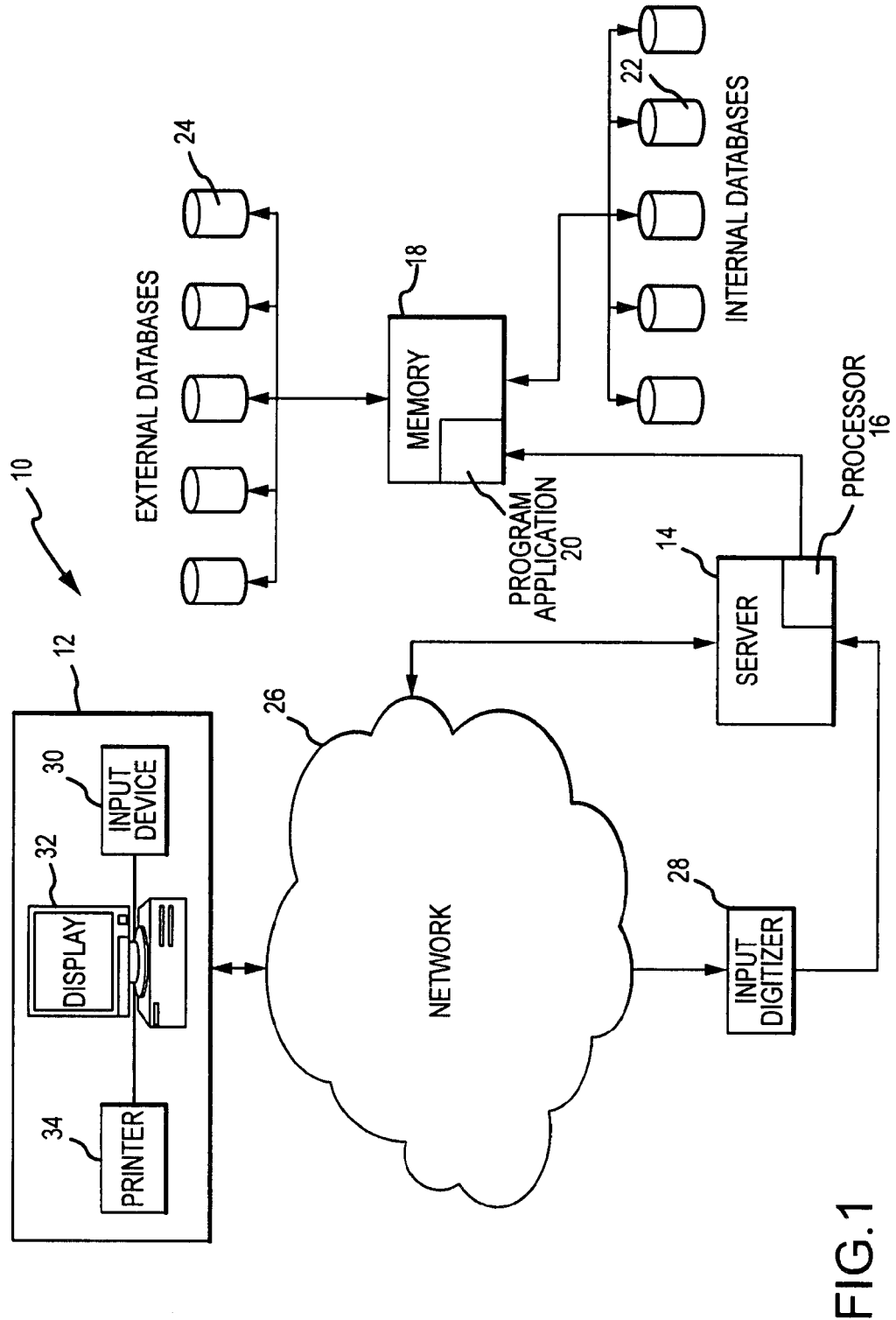
FIG. 1 illustrates a block diagram of an exemplary embodiment of a system for determining individualized medical intervention for a particular disease state that utilizes molecular profiling of a patient's biological specimen that is non disease specific.

The detailed description of exemplary embodiments herein makes reference to the accompanying drawings and pictures, which show the exemplary embodiment by way of illustration and its best mode. While these exemplary embodiments are described in sufficient detail to enable those skilled in the art to practice the invention, it should be understood that other embodiments may be realized and that logical and mechanical changes may be made without departing from the spirit and scope of the invention. Thus, the detailed description herein is presented for purposes of illustration only and not of limitation. For example, the steps recited in any of the method or process descriptions may be executed in any order and are not limited to the order presented. Moreover, any of the functions or steps may be outsourced to or performed by one or more third parties. Furthermore, any reference to singular includes plural embodiments, and any reference to more than one component may include a singular embodiment.

For the sake of brevity, conventional data networking, application development and other functional aspects of the systems (and components of the individual operating components of the systems) may not be described in detail herein. Furthermore, the connecting lines shown in the various figures contained herein are intended to represent exemplary functional relationships and/or physical couplings between the various elements. It should be noted that many alternative or additional functional relationships or physical connections may be present in a practical system.

The various system components discussed herein may include one or more of the following: a host server or other computing systems including a processor for processing digital data; a memory coupled to the processor for storing digital data; an input digitizer coupled to the processor for inputting digital data; an application program stored in the memory and accessible by the processor for directing processing of digital data by the processor; a display device coupled to the processor and memory for displaying information derived from digital data processed by the processor; and a plurality of databases. Various databases used herein may include: patient data such as family history, demography and environmental data, biological sample data, prior treatment and protocol data, patient clinical data, molecular profiling data of biological samples, data on therapeutic drug agents and/or investigative drugs, a gene library, a disease library, a drug library, patient tracking data, file management data, financial management data, billing data and/or like data useful in the operation of the system. As those skilled in the art will appreciate, user computer may include an operating system (e.g., Windows NT, 95/98/2000, OS2, UNIX, Linux, Solaris, MacOS, etc.) as well as various conventional support software and drivers typically associated with computers. The computer may include any suitable personal computer, network computer, workstation, minicomputer, mainframe or the like. User computer can be in a home or medical/business environment with access to a network. In an exemplary embodiment, access is through a network or the Internet through a commercially-available web-browser software package.

As used herein, the term "network" shall include any electronic communications means which incorporates both hardware and software components of such. Communication among the parties may be accomplished through any suitable communication channels, such as, for example, a telephone network, an extranet, an intranet, Internet, point of interaction device, personal digital assistant (e.g., Palm Pilot®, Blackberry®), cellular phone, kiosk, etc.), online communications, satellite communications, off-line communications, wireless communications, transponder communications, local area network (LAN), wide area network (WAN), networked or linked devices, keyboard, mouse and/or any suitable communication or data input modality. Moreover, although the system is frequently described herein as being implemented with TCP/IP communications protocols, the system may also be implemented using IPX, Appletalk, IP-6, NetBIOS, OSI or any number of existing or future protocols. If the network is in the nature of a public network, such as the Internet, it may be advantageous to presume the network to be insecure and open to eavesdroppers. Specific information related to the protocols, standards, and application software utilized in connection with the Internet is generally known to those skilled in the art and, as such, need not be detailed herein. See, for example, DILIP NAIK, INTERNET STANDARDS AND PROTOCOLS (1998); JAVA 2 COMPLETE, various authors, (Sybex 1999); DEBORAH RAY AND ERIC RAY, MASTERING HTML 4.0 (1997); and LOSHIN, TCP/IP CLEARLY EXPLAINED (1997) and DAVID GOURLEY AND BRIAN TOTTY, HTTP, THE DEFINITIVE GUIDE (2002), the contents of which are hereby incorporated by reference.

The various system components may be independently, separately or collectively suitably coupled to the network via data links which includes, for example, a connection to an Internet Service Provider (ISP) over the local loop as is typically used in connection with standard modem communication, cable modem, Dish networks, ISDN, Digital Subscriber Line (DSL), or various wireless communication methods, see, e.g., GILBERT HELD, UNDERSTANDING DATA COMMUNICATIONS (1996), which is hereby incorporated by reference. It is noted that the network may be implemented as other types of networks, such as an interactive television (ITV) network. Moreover, the system contemplates the use, sale or distribution of any goods, services or information over any network having similar functionality described herein.

As used herein, "transmit" may include sending electronic data from one system component to another over a network connection. Additionally, as used herein, "data" may include encompassing information such as commands, queries, files, data for storage, and the like in digital or any other form.

The system contemplates uses in association with web services, utility computing, pervasive and individualized computing, security and identity solutions, autonomic computing, commodity computing, mobility and wireless solutions, open source, biometrics, grid computing and/or mesh computing.

Any databases discussed herein may include relational, hierarchical, graphical, or object-oriented structure and/or any other database configurations. Common database products that may be used to implement the databases include DB2 by IBM (White Plains, N.Y.), various database products available from Oracle Corporation (Redwood Shores, Calif.), Microsoft Access or Microsoft SQL Server by Microsoft Corporation (Redmond, Wash.), or any other suitable database product. Moreover, the databases may be organized in any suitable manner, for example, as data tables or lookup tables. Each record may be a single file, a series of files, a linked series of data fields or any other data structure. Association of certain data may be accomplished through any desired data association technique such as those known or practiced in the art. For example, the association may be accomplished either manually or automatically. Automatic association techniques may include, for example, a database search, a database merge, GREP, AGREP, SQL, using a key field in the tables to speed searches, sequential searches through all the tables and files, sorting records in the file according to a known order to simplify lookup, and/or the like. The association step may be accomplished by a database merge function, for example, using a "key field" in pre-selected databases or data sectors.

More particularly, a "key field" partitions the database according to the high-level class of objects defined by the key field. For example, certain types of data may be designated as a key field in a plurality of related data tables and the data tables may then be linked on the basis of the type of data in the key field. The data corresponding to the key field in each of the linked data tables is preferably the same or of the same type. However, data tables having similar, though not identical, data in the key fields may also be linked by using AGREP, for example. In accordance with one embodiment, any suitable data storage technique may be utilized to store data without a standard format. Data sets may be stored using any suitable technique, including, for example, storing individual files using an ISO/IEC 7816-4 file structure; implementing a domain whereby a dedicated file is selected that exposes one or more elementary files containing one or more data sets; using data sets stored in individual files using a hierarchical filing system; data sets stored as records in a single file (including compression, SQL accessible, hashed via one or more keys, numeric, alphabetical by first tuple, etc.); Binary Large Object (BLOB); stored as ungrouped data elements encoded using ISO/IEC 7816-6 data elements; stored as ungrouped data elements encoded using ISO/IEC Abstract Syntax Notation (ASN.1) as in ISO/IEC 8824 and 8825; and/or other proprietary techniques that may include fractal compression methods, image compression methods, etc.

In one exemplary embodiment, the ability to store a wide variety of information in different formats is facilitated by storing the information as a BLOB. Thus, any binary information can be stored in a storage space associated with a data set. The BLOB method may store data sets as ungrouped data elements formatted as a block of binary via a fixed memory offset using either fixed storage allocation, circular queue techniques, or best practices with respect to memory management (e.g., paged memory, least recently used, etc.). By using BLOB methods, the ability to store various data sets that have different formats facilitates the storage of data by multiple and unrelated owners of the data sets. For example, a first data set which may be stored may be provided by a first party, a second data set which may be stored may be provided by an unrelated second party, and yet a third data set which may be stored, may be provided by a third party unrelated to the first and second party. Each of these three exemplary data sets may contain different information that is stored using different data storage formats and/or techniques. Further, each data set may contain subsets of data that also may be distinct from other subsets.

As stated above, in various embodiments, the data can be stored without regard to a common format. However, in one exemplary embodiment, the data set (e.g., BLOB) may be annotated in a standard manner when provided for manipulating the data. The annotation may comprise a short header, trailer, or other appropriate indicator related to each data set that is configured to convey information useful in managing the various data sets. For example, the annotation may be called a "condition header", "header", "trailer", or "status", herein, and may comprise an indication of the status of the data set or may include an identifier correlated to a specific issuer or owner of the data. Subsequent bytes of data may be used to indicate for example, the identity of the issuer or owner of the data, user, transaction/membership account identifier or the like. Each of these condition annotations are further discussed herein.

The data set annotation may also be used for other types of status information as well as various other purposes. For example, the data set annotation may include security information establishing access levels. The access levels may, for example, be configured to permit only certain individuals, levels of employees, companies, or other entities to access data sets, or to permit access to specific data sets based on the transaction, issuer or owner of data, user or the like. Furthermore, the security information may restrict/permit only certain actions such as accessing, modifying, and/or deleting data sets. In one example, the data set annotation indicates that only the data set owner or the user are permitted to delete a data set, various identified users may be permitted to access the data set for reading, and others are altogether excluded from accessing the data set. However, other access restriction parameters may also be used allowing various entities to access a data set with various permission levels as appropriate. The data, including the header or trailer may be received by a stand alone interaction device configured to add, delete, modify, or augment the data in accordance with the header or trailer.

One skilled in the art will also appreciate that, for security reasons, any databases, systems, devices, servers or other components of the system may consist of any combination thereof at a single location or at multiple locations, wherein each database or system includes any of various suitable security features, such as firewalls, access codes, encryption, decryption, compression, decompression, and/or the like.

The computing unit of the web client may be further equipped with an Internet browser connected to the Internet or an intranet using standard dial-up, cable, DSL or any other Internet protocol known in the art. Transactions originating at a web client may pass through a firewall in order to prevent unauthorized access from users of other networks. Further, additional firewalls may be deployed between the varying components of CMS to further enhance security.

Firewall may include any hardware and/or software suitably configured to protect CMS components and/or enterprise computing resources from users of other networks. Further, a firewall may be configured to limit or restrict access to various systems and components behind the firewall for web clients connecting through a web server. Firewall may reside in varying configurations including Stateful Inspection, Proxy based and Packet Filtering among others. Firewall may be integrated within an web server or any other CMS components or may further reside as a separate entity.

The computers discussed herein may provide a suitable website or other Internet-based graphical user interface which is accessible by users. In one embodiment, the Microsoft Internet Information Server (IIS), Microsoft Transaction Server (MTS), and Microsoft SQL Server, are used in conjunction with the Microsoft operating system, Microsoft NT web server software, a Microsoft SQL Server database system, and a Microsoft Commerce Server. Additionally, components such as Access or Microsoft SQL Server, Oracle, Sybase, Informix MySQL, Interbase, etc., may be used to provide an Active Data Object (ADO) compliant database management system.

Any of the communications, inputs, storage, databases or displays discussed herein may be facilitated through a website having web pages. The term "web page" as it is used herein is not meant to limit the type of documents and applications that might be used to interact with the user. For example, a typical website might include, in addition to standard HTML documents, various forms, Java applets, JavaScript, active server pages (ASP), common gateway interface scripts (CGI), extensible markup language (XML), dynamic HTML, cascading style sheets (CSS), helper applications, plug-ins, and the like. A server may include a web service that receives a request from a web server, the request including a URL (yahoo.com/stockquotes/ge) and an IP address (123.56.789.234). The web server retrieves the appropriate web pages and sends the data or applications for the web pages to the IP address. Web services are applications that are capable of interacting with other applications over a communications means, such as the internet. Web services are typically based on standards or protocols such as XML, XSLT, SOAP, WSDL and UDDI. Web services methods are well known in the art, and are covered in many standard texts. See, e.g., ALEX NGHIEM, IT WEB SERVICES: A ROADMAP FOR THE ENTERPRISE (2003), hereby incorporated by reference.

The web-based clinical database for the system and method of the present invention preferably has the ability to upload and store clinical data files in native formats and is searchable on any clinical parameter. The database is also scalable and may utilize an EAV data model (metadata) to enter clinical annotations from any study for easy integration with other studies. In addition, the web-based clinical database is flexible and may be XML and XSLT enabled to be able to add user customized questions dynamically. Further, the database includes exportability to CDISC ODM.

Practitioners will also appreciate that there are a number of methods for displaying data within a browser-based document. Data may be represented as standard text or within a fixed list, scrollable list, drop-down list, editable text field, fixed text field, pop-up window, and the like. Likewise, there are a number of methods available for modifying data in a web page such as, for example, free text entry using a keyboard, selection of menu items, check boxes, option boxes, and the like.

The system and method may be described herein in terms of functional block components, screen shots, optional selections and various processing steps. It should be appreciated that such functional blocks may be realized by any number of hardware and/or software components configured to perform the specified functions. For example, the system may employ various integrated circuit components, e.g., memory elements, processing elements, logic elements, look-up tables, and the like, which may carry out a variety of functions under the control of one or more microprocessors or other control devices. Similarly, the software elements of the system may be implemented with any programming or scripting language such as C, C++, Macromedia Cold Fusion, Microsoft Active Server Pages, Java, COBOL, assembler, PERL, Visual Basic, SQL Stored Procedures, extensible markup language (XML), with the various algorithms being implemented with any combination of data structures, objects, processes, routines or other programming elements. Further, it should be noted that the system may employ any number of conventional techniques for data transmission, signaling, data processing, network control, and the like. Still further, the system could be used to detect or prevent security issues with a client-side scripting language, such as JavaScript, VBScript or the like. For a basic introduction of cryptography and network security, see any of the following references: (1) "Applied Cryptography: Protocols, Algorithms, And Source Code In C," by Bruce Schneier, published by John Wiley & Sons (second edition, 1995); (2) "Java Cryptography" by Jonathan Knudson, published by O'Reilly & Associates (1998); (3) "Cryptography & Network Security: Principles & Practice" by William Stallings, published by Prentice Hall; all of which are hereby incorporated by reference.

As used herein, the term "end user", "consumer", "customer", "client", "treating physician", "hospital", or "business" may be used interchangeably with each other, and each shall mean any person, entity, machine, hardware, software or business. Each participant is equipped with a computing device in order to interact with the system and facilitate online data access and data input. The customer has a computing unit in the form of a personal computer, although other types of computing units may be used including laptops, notebooks, hand held computers, set-top boxes, cellular telephones, touch-tone telephones and the like. The owner/operator of the system and method of the present invention has a computing unit implemented in the form of a computer-server, although other implementations are contemplated by the system including a computing center shown as a main frame computer, a minicomputer, a PC server, a network of computers located in the same of different geographic locations, or the like. Moreover, the system contemplates the use, sale or distribution of any goods, services or information over any network having similar functionality described herein.

In one exemplary embodiment, each client customer may be issued an "account" or "account number". As used herein, the account or account number may include any device, code, number, letter, symbol, digital certificate, smart chip, digital signal, analog signal, biometric or other identifier/indicia suitably configured to allow the consumer to access, interact with or communicate with the system (e.g., one or more of an authorization/access code, personal identification number (PIN), Internet code, other identification code, and/or the like). The account number may optionally be located on or associated with a charge card, credit card, debit card, prepaid card, embossed card, smart card, magnetic stripe card, bar code card, transponder, radio frequency card or an associated account. The system may include or interface with any of the foregoing cards or devices, or a fob having a transponder and RFID reader in RF communication with the fob. Although the system may include a fob embodiment, the invention is not to be so limited. Indeed, system may include any device having a transponder which is configured to communicate with RFID reader via RF communication. Typical devices may include, for example, a key ring, tag, card, cell phone, wristwatch or any such form capable of being presented for interrogation. Moreover, the system, computing unit or device discussed herein may include a "pervasive computing device," which may include a traditionally non-computerized device that is embedded with a computing unit. The account number may be distributed and stored in any form of plastic, electronic, magnetic, radio frequency, wireless, audio and/or optical device capable of transmitting or downloading data from itself to a second device.

As will be appreciated by one of ordinary skill in the art, the system may be embodied as a customization of an existing system, an add-on product, upgraded software, a stand alone system, a distributed system, a method, a data processing system, a device for data processing, and/or a computer program product. Accordingly, the system may take the form of an entirely software embodiment, an entirely hardware embodiment, or an embodiment combining aspects of both software and hardware. Furthermore, the system may take the form of a computer program product on a computer-readable storage medium having computer-readable program code means embodied in the storage medium. Any suitable computer-readable storage medium may be utilized, including hard disks, CD-ROM, optical storage devices, magnetic storage devices, and/or the like.

The system and method is described herein with reference to screen shots, block diagrams and flowchart illustrations of methods, apparatus (e.g., systems), and computer program products according to various embodiments. It will be understood that each functional block of the block diagrams and the flowchart illustrations, and combinations of functional blocks in the block diagrams and flowchart illustrations, respectively, can be implemented by computer program instructions.

Referring now to FIGS. 2-25 the process flows and screenshots depicted are merely embodiments and are not intended to limit the scope of the invention as described herein. For example, the steps recited in any of the method or process descriptions may be executed in any order and are not limited to the order presented. It will be appreciated that the following description makes appropriate references not only to the steps and user interface elements depicted in FIGS. 2-25, but also to the various system components as described above with reference to FIG. 1.

These computer program instructions may be loaded onto a general purpose computer, special purpose computer, or other programmable data processing apparatus to produce a machine, such that the instructions that execute on the computer or other programmable data processing apparatus create means for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions specified in the flowchart block or blocks.

Accordingly, functional blocks of the block diagrams and flowchart illustrations support combinations of means for performing the specified functions, combinations of steps for performing the specified functions, and program instruction means for performing the specified functions. It will also be understood that each functional block of the block diagrams and flowchart illustrations, and combinations of functional blocks in the block diagrams and flowchart illustrations, can be implemented by either special purpose hardware-based computer systems which perform the specified functions or steps, or suitable combinations of special purpose hardware and computer instructions. Further, illustrations of the process flows and the descriptions thereof may make reference to user windows, webpages, websites, web forms, prompts, etc. Practitioners will appreciate that the illustrated steps described herein may comprise in any number of configurations including the use of windows, webpages, web forms, popup windows, prompts and the like. It should be further appreciated that the multiple steps as illustrated and described may be combined into single webpages and/or windows but have been expanded for the sake of simplicity. In other cases, steps illustrated and described as single process steps may be separated into multiple webpages and/or windows but have been combined for simplicity.

Benefits, other advantages, and solutions to problems have been described herein with regard to specific embodiments. However, the benefits, advantages, solutions to problems, and any element(s) that may cause any benefit, advantage, or solution to occur or become more pronounced are not to be construed as critical, required, or essential features or elements of any or all the claims or the invention. The scope of the invention is accordingly to be limited by nothing other than the appended claims, in which reference to an element in the singular is not intended to mean "one and only one" unless explicitly so stated, but rather "one or more." All structural, chemical, and functional equivalents to the elements of the above-described exemplary embodiments that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for." As used herein, the terms "comprises", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus. Further, no element described herein is required for the practice of the invention unless expressly described as "essential" or "critical".

FIG. 1 is a block diagram of an exemplary embodiment of a system 10 for determining individualized medical intervention for a particular disease state that utilizes molecular profiling of a patient's biological specimen. System 10 includes a user interface 12, a host server 14 including a processor 16 for processing data, a memory 18 coupled to the processor, an application program 20 stored in the memory 18 and accessible by the processor 16 for directing processing of the data by the processor 16, a plurality of internal databases 22 and external databases 24, and an interface with a wired or wireless communications network 26 (such as the Internet, for example). System 10 may also include an input digitizer 28 coupled to the processor 16 for inputting digital data from data that is received from user interface 12.

User interface 12 includes an input device 30 and a display 32 for inputting data into system 10 and for displaying information derived from the data processed by processor 16. User interface 12 may also include a printer 34 for printing the information derived from the data processed by the processor 16 such as patient reports that may include test results for targets and proposed drug therapies based on the test results.

Internal databases 22 may include, but are not limited to, patient biological sample/specimen information and tracking, clinical data, patient data, patient tracking, file management, study protocols, patient test results from molecular profiling, and billing information and tracking. External databases 24 may include, but are not limited to, drug libraries, gene libraries, disease libraries, and public and private databases such as UniGene, OMIM, GO, TIGR, GenBank, KEGG and Biocarta.

Figure 2:
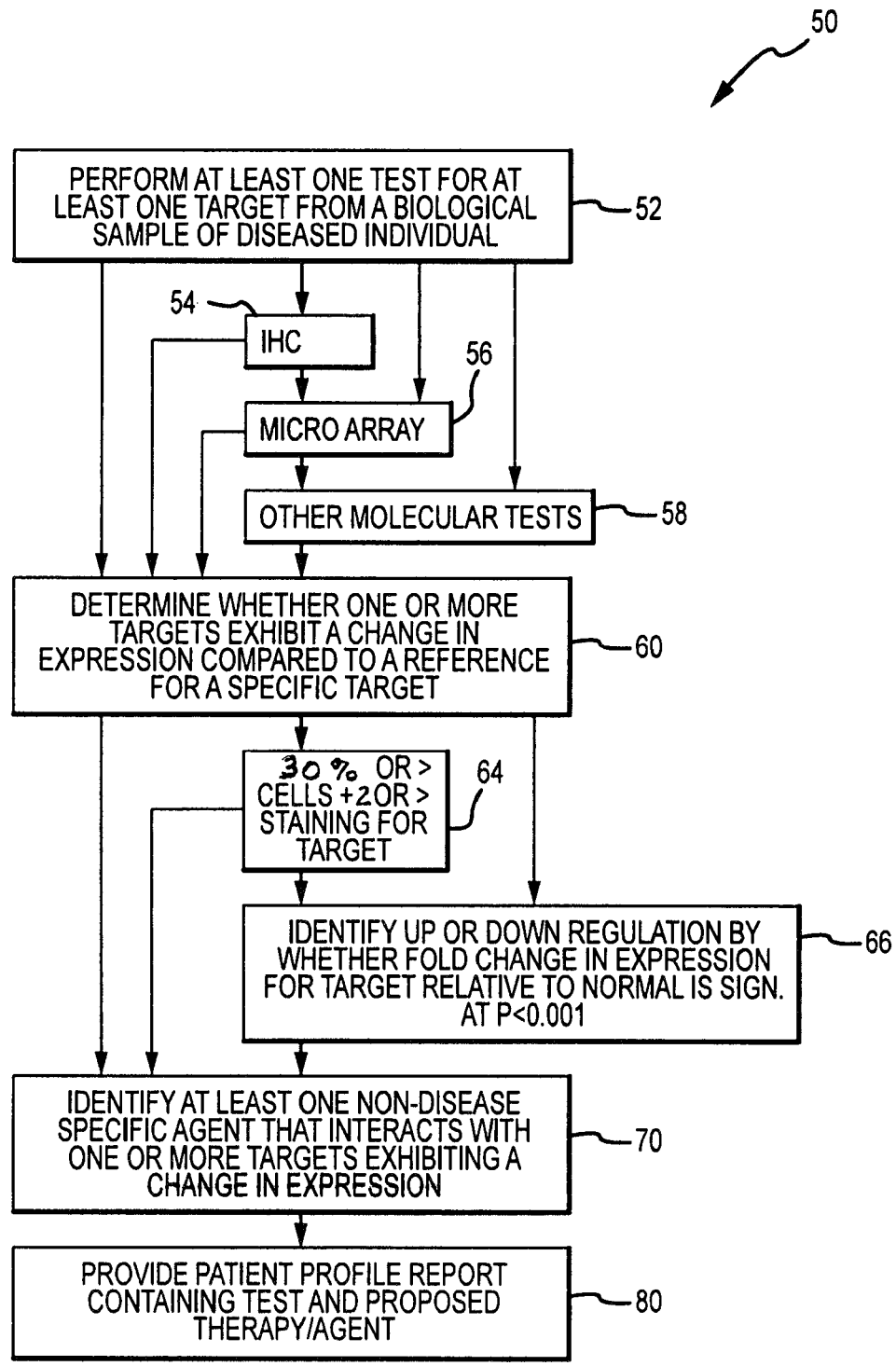
FIG. 2 is a flowchart of an exemplary embodiment of a method for determining individualized medical intervention for a particular disease state that utilizes molecular profiling of a patient's biological specimen that is non disease specific.

Various methods may be used in accordance with system 10. FIG. 2 shows a flowchart of an exemplary embodiment of a method 50 for determining individualized medical intervention for a particular disease state that utilizes molecular profiling of a patient's biological specimen that is non disease specific. In order to determine a medical intervention for a particular disease state using molecular profiling that is independent of disease lineage diagnosis (i.e. not single disease restricted), at least one test is performed for at least one target from a biological sample of a diseased patient in step 52. A target is defined as any molecular finding that may be obtained from molecular testing. For example, a target may include one or more genes, one or more gene expressed proteins, one or more molecular mechanisms, and/or combinations of such. Tests for finding such targets may include, but are not limited to an immunohistochemical (IHC) analysis, a micro array analysis such as a comparative genomic hybridization (CGH) micro array, a single nucleotide polymorphism (SNP) micro array, a fluorescent in-situ hybridization (FISH), an in-situ hybridization (ISH), and a proteomic array, and other molecular tests known to those skilled in the art. Accordingly, one or more of the following may be performed: an IHC analysis in step 54, a microanalysis in step 56, and other molecular tests know to those skilled in the art in step 58.

Biological samples are obtained from diseased patients by taking a biopsy of a tumor, conducting minimally invasive surgery if no recent tumor is available, obtaining a sample of the patient's blood, or a sample of any other biological fluid including, but not limited to, cell extracts, nuclear extracts, cell lysates or biological products or substances of biological origin such as excretions, blood, sera, plasma, urine, sputum, tears, feces, saliva, membrane extracts, and the like.

In step 60, a determination is made as to whether one or more of the targets that were tested for in step 52 exhibit a change in expression compared to a normal reference for that particular target. In one exemplary method of the invention, an IHC analysis may be performed in step 54 and a determination as to whether any targets from the IHC analysis exhibit a change in expression is made in step 64 by determining whether 30% or more of the biological sample cells were +2 or greater staining for the particular target. It will be understood by those skilled in the art that there will be instances where +1 or greater staining will indicate a change in expression in that staining results may vary depending on the technician performing the test and type of target being tested. In another exemplary embodiment of the invention, a micro array analysis may be performed in step 56 and a determination as to whether any targets from the micro array analysis exhibit a change in expression is made in step 66 by identifying which targets are up-regulated or down-regulated by determining whether the fold change in expression for a particular target relative to a normal tissue of origin reference is significant at $p<0.001$. A change in expression may also be evidenced by an absence of one or more genes, gene expressed proteins, molecular mechanisms, or other molecular findings.

After determining which targets exhibit a change in expression in step 60, at least one non-disease specific agent is identified that interacts with each target having a changed expression in step 70. An agent may be any drug or compound having a therapeutic effect. A non-disease specific agent is a therapeutic drug or compound not previously associated with treating the patient's diagnosed disease that is capable of interacting with the target from the patient's biological sample that has exhibited a change in expression. Some of the non-disease specific agents that have been found to interact with specific targets found in different cancer patients are shown in Table 1 below.

TABLE 1

| Patients | Target(s) Found | Treatment(s) |
| --- | --- | --- |
| Advanced Pancreatic Cancer | HER 2/neu (IHC/Array) | Herceptin ™ |
| Advanced Pancreatic Cancer | EGFR (IHC), HIF 1α | Erbitux ™, Rapamycin ™ |
| Advanced Ovarian Cancer | ERCC3 (Array) | Irofulvene |
| Advanced Adenoid Cystic Carcinoma | Vitamin D receptors, Androgen receptors | Calcitriol ™, Flutamide ™ |

Finally, in step 80, a patient profile report may be provided which includes the patient's test results for various targets and any proposed therapies based on those results. An exemplary patient profile report 100 is shown in FIGS. 3A-3D. Patient profile report 100 shown in FIG. 3A identifies the targets tested 102, those targets tested that exhibited significant changes in expression 104, and proposed non-disease specific agents for interacting with the targets 106. Patient profile report 100 shown in FIG. 3B identifies the results 108 of immunohistochemical analysis for certain gene expressed proteins 110 and whether a gene expressed protein is a molecular target 112 by determining whether 30% or more of the tumor cells were +2 or greater staining Report 100 also identifies immunohistochemical tests that were not performed 114. Patient profile report 100 shown in FIG. 3C identifies the genes analyzed 116 with a micro array analysis and whether the genes were under expressed or over expressed 118 compared to a reference. Finally, patient profile report 100 shown in FIG. 3D identifies the clinical history 120 of the patient and the specimens that were submitted 122 from the patient.

Figure 4:
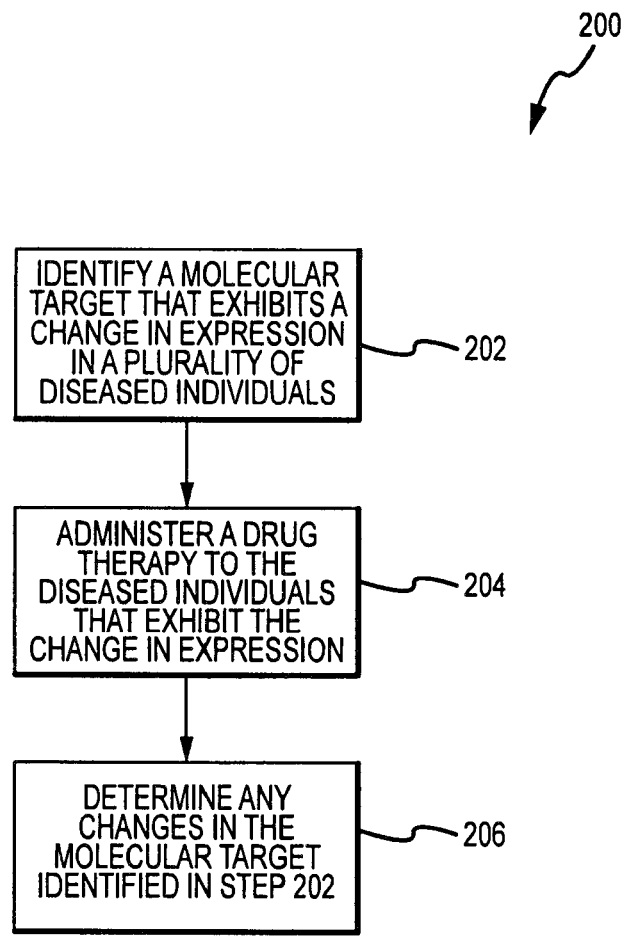
FIG. 4 is a flowchart of an exemplary embodiment of a method for identifying a drug therapy/agent capable of interacting with a target.

FIG. 4 shows a flowchart of an exemplary embodiment of a method 200 for identifying a drug therapy/agent capable of interacting with a target. In step 202, a molecular target is identified which exhibits a change in expression in a number of diseased individuals. Next, in step 204, a drug therapy/agent is administered to the diseased individuals. After drug therapy/agent administration, any changes in the molecular target identified in step 202 are identified in step 206 in order to determine if the drug therapy/agent administered in step 204 interacts with the molecular targets identified in step 202. If it is determined that the drug therapy/agent administered in step 204 interacts with a molecular target identified in step 202, the drug therapy/agent may be approved for treating patients exhibiting a change in expression of the identified molecular target instead of approving the drug therapy/agent for a particular disease.

Figure 5:
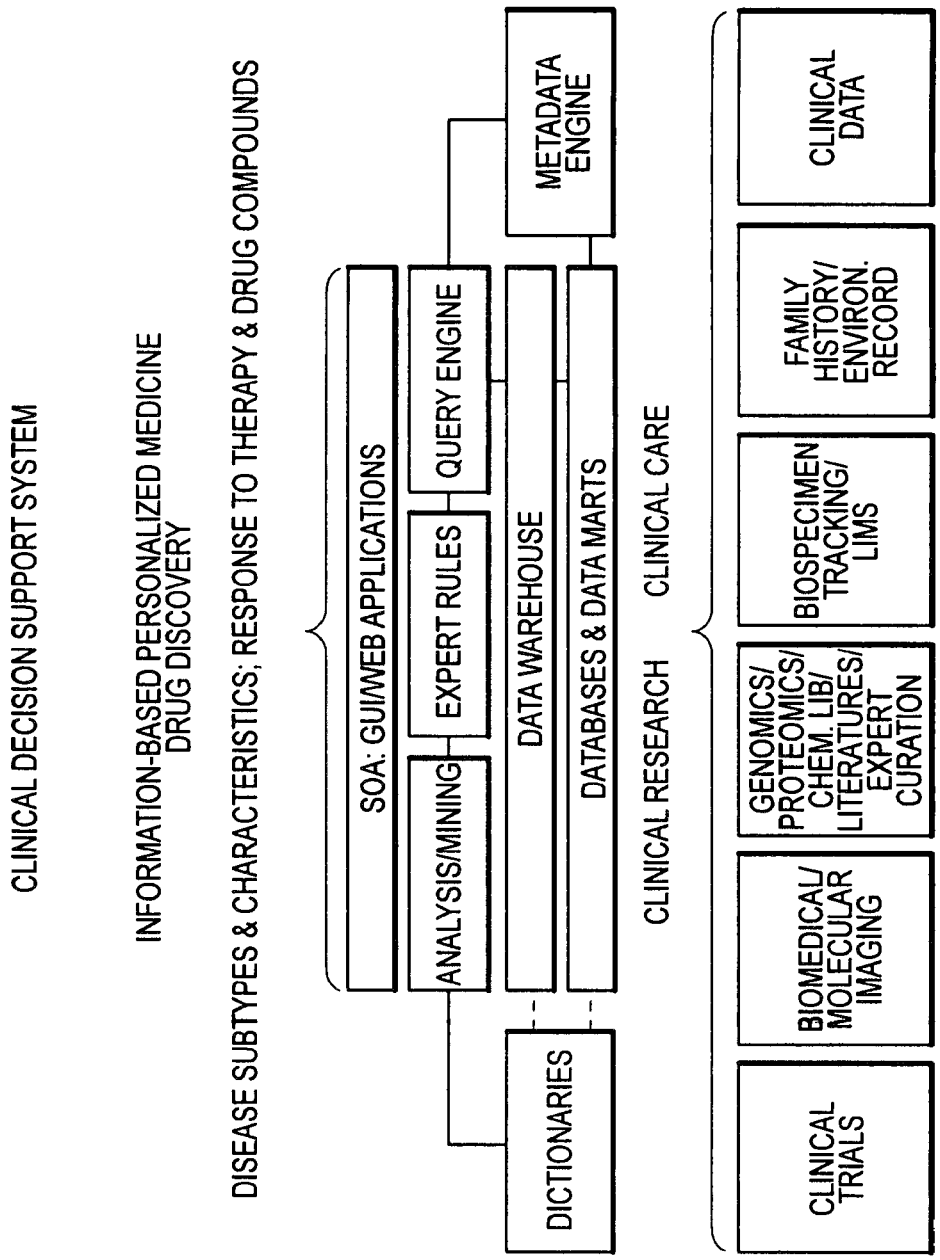
FIGS. 5-14 are flowcharts and diagrams illustrating various parts of an information-based personalized medicine drug discovery system and method in accordance with the present invention.
Figure 6:
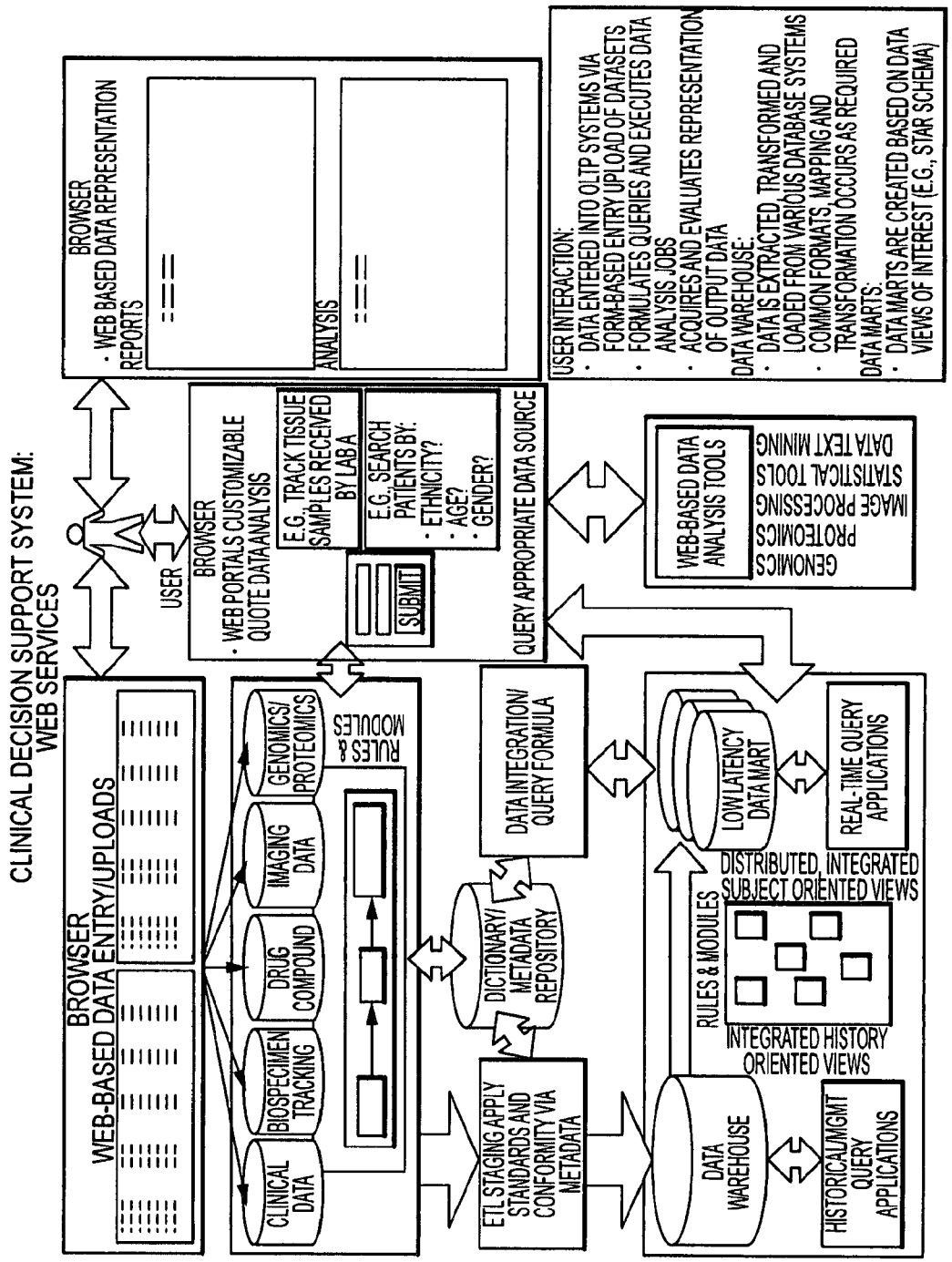

FIGS. 5-14 are flowcharts and diagrams illustrating various parts of an information-based personalized medicine drug discovery system and method in accordance with the present invention. FIG. 5 is a diagram showing an exemplary clinical decision support system of the information-based personalized medicine drug discovery system and method of the present invention. Data obtained through clinical research and clinical care such as clinical trial data, biomedical/molecular imaging data, genomics/proteomics/chemical library/literature/expert curation, biospecimen tracking/LIMS, family history/environmental records, and clinical data are collected and stored as databases and datamarts within a data warehouse. FIG. 6 is a diagram showing the flow of information through the clinical decision support system of the information-based personalized medicine drug discovery system and method of the present invention using web services. A user interacts with the system by entering data into the system via form-based entry/upload of data sets, formulating queries and executing data analysis jobs, and acquiring and evaluating representations of output data. The data warehouse in the web based system is where data is extracted, transformed, and loaded from various database systems. The data warehouse is also where common formats, mapping and transformation occurs. The web based system also includes datamarts which are created based on data views of interest.

Figure 7:
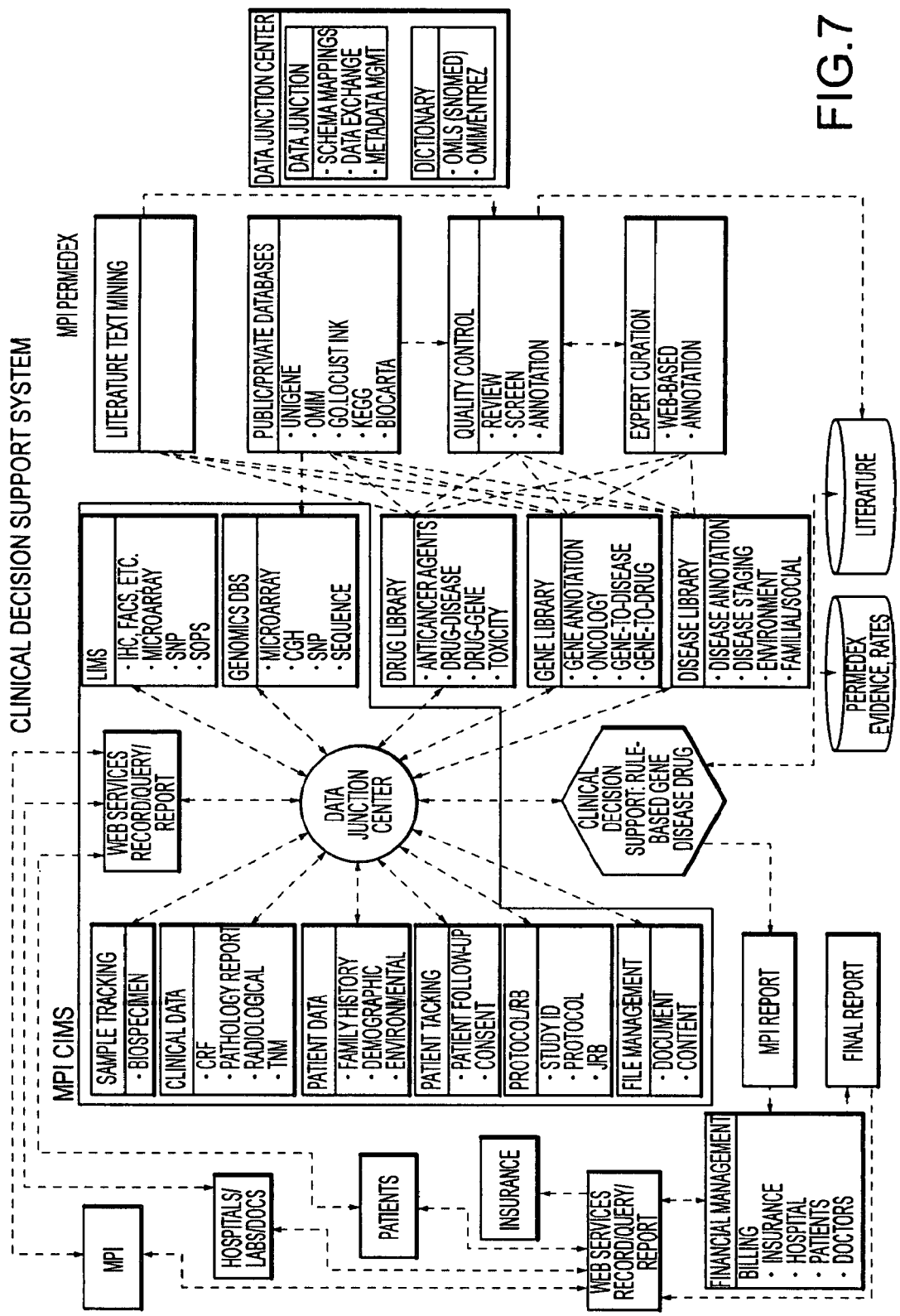

A flow chart of an exemplary clinical decision support system of the information-based personalized medicine drug discovery system and method of the present invention is shown in FIG. 7. The clinical information management system includes the laboratory information management system and the medical information contained in the data warehouses and databases includes medical information libraries, such as drug libraries, gene libraries, and disease libraries, in addition to literature text mining Both the information management systems relating to particular patients and the medical information databases and data warehouses come together at a data junction center where diagnostic information and therapeutic options can be obtained. A financial management system may also be incorporated in the clinical decision support system of the information-based personalized medicine drug discovery system and method of the present invention.

Figure 8:
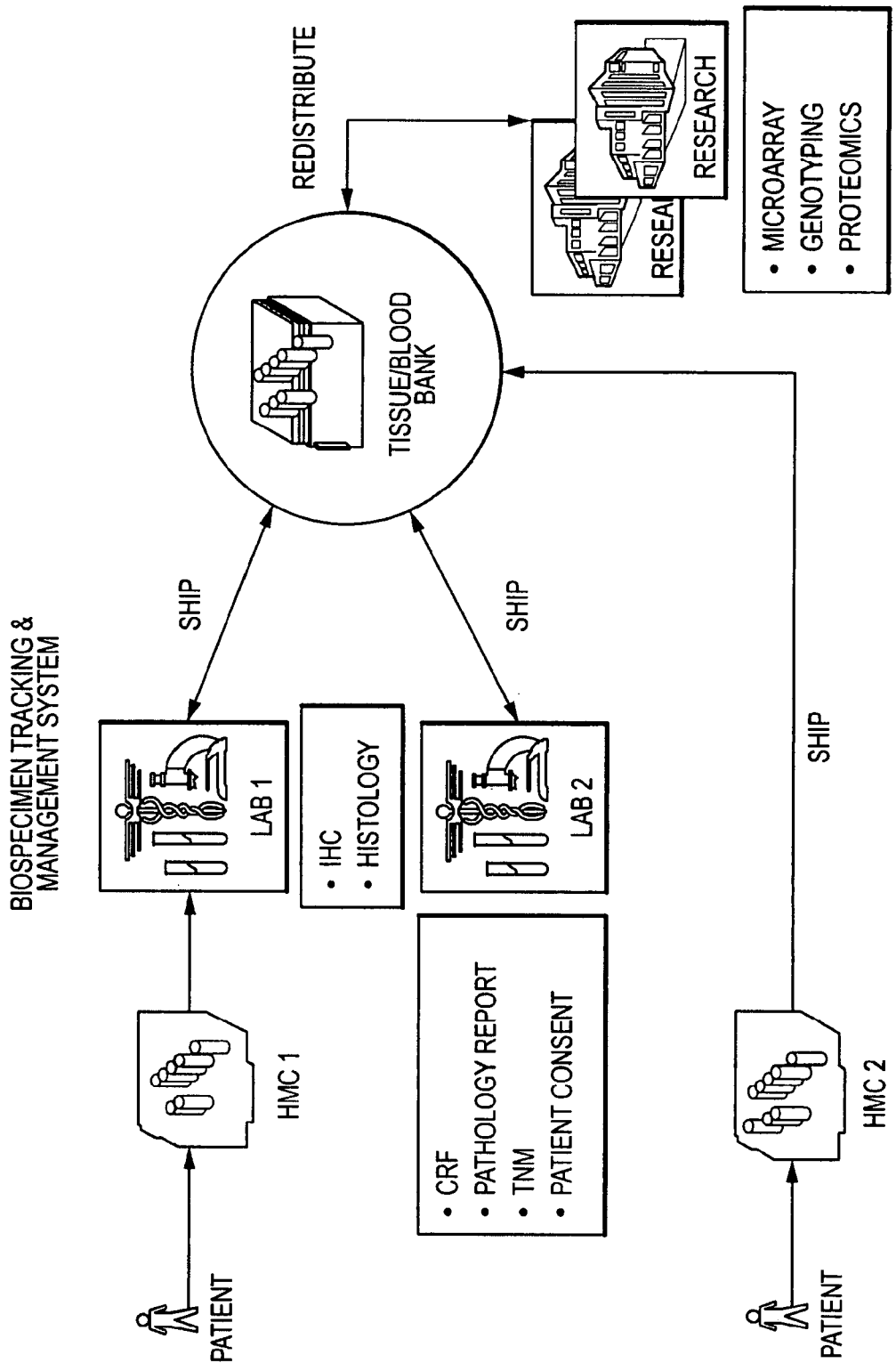
Figure 9:
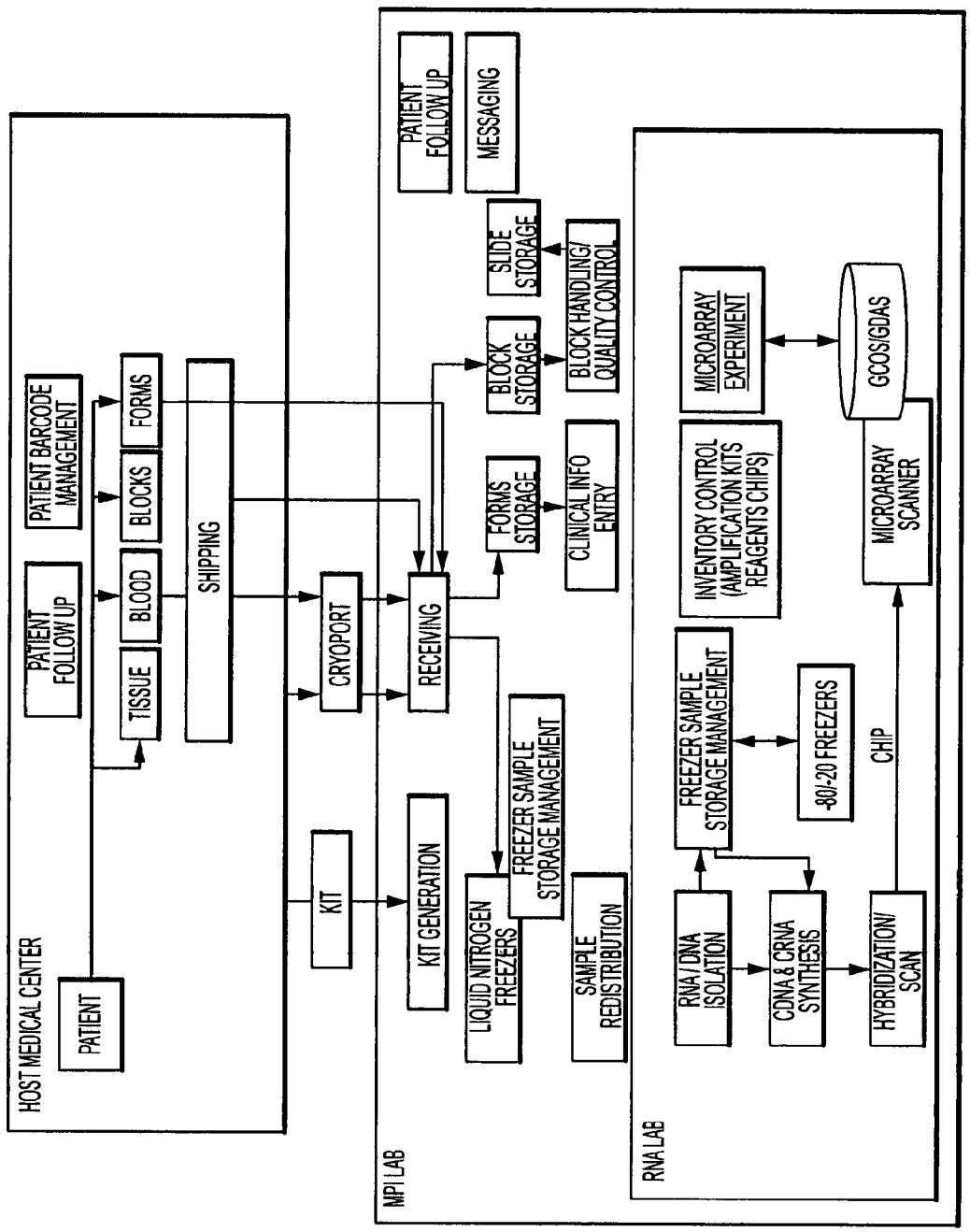

FIG. 8 is a diagram showing an exemplary biospecimen tracking and management system which may be utilized as part of the information-based personalized medicine drug discovery system and method of the present invention. FIG. 8 shows two host medical centers which forward specimens to a tissue/blood bank. The specimens may go through laboratory analysis prior to shipment. Research may also be conducted on the samples via micro array, genotyping, and proteomic analysis. This information can be redistributed to the tissue/blood bank. FIG. 9 depicts a flow chart of an exemplary biospecimen tracking and management system which may be utilized with the information-based personalized medicine drug discovery system and method of the present invention. The host medical center obtains samples from patients and then ships the patient samples to a molecular profiling laboratory which may also perform RNA and DNA isolation and analysis.

Figure 10:
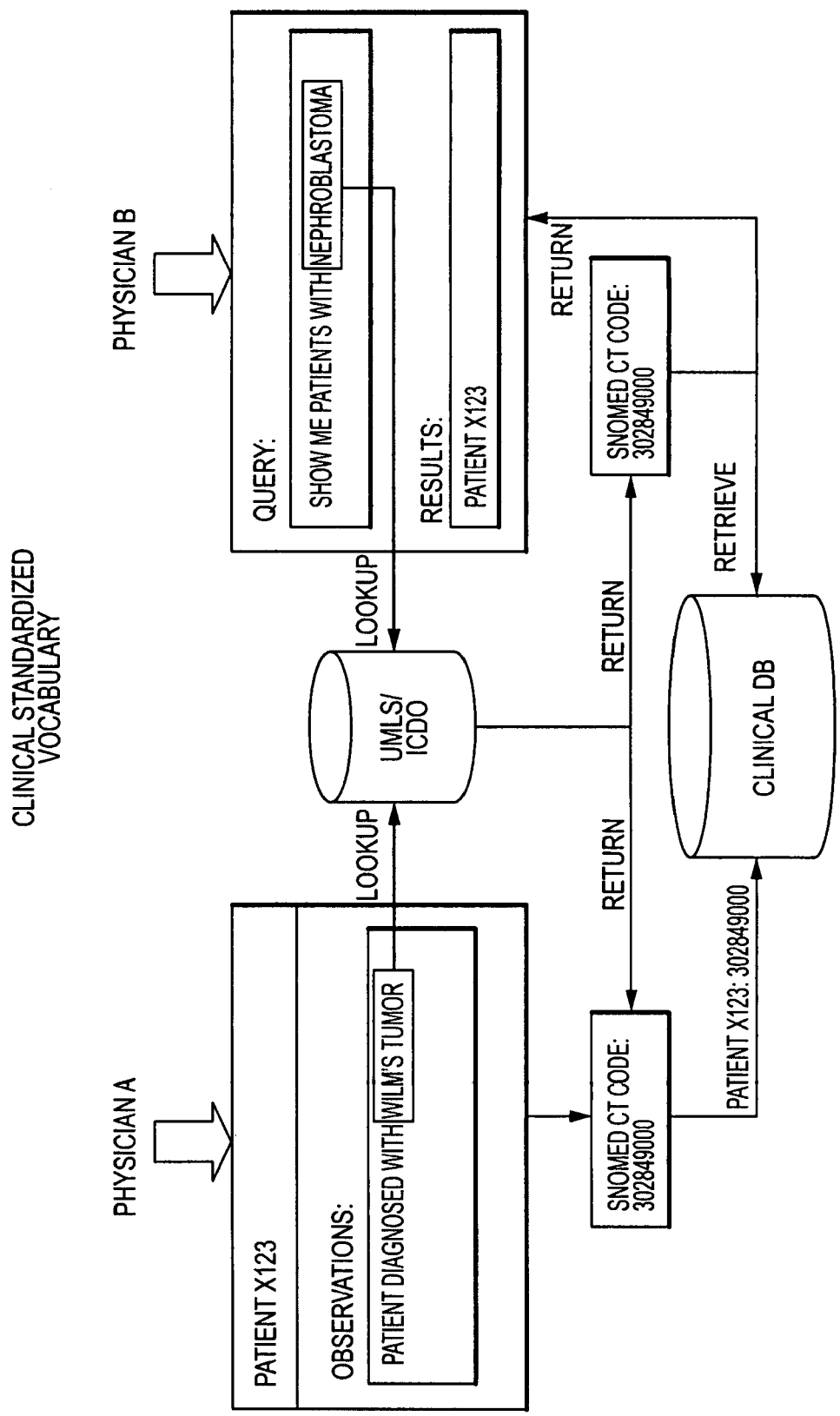

A diagram showing a method for maintaining a clinical standardized vocabulary for use with the information-based personalized medicine drug discovery system and method of the present invention is shown in FIG. 10. FIG. 10 illustrates how physician observations and patient information associated with one physician's patient may be made accessible to another physician to enable the other physician to utilize the data in making diagnostic and therapeutic decisions for their patients.

Figure 11:
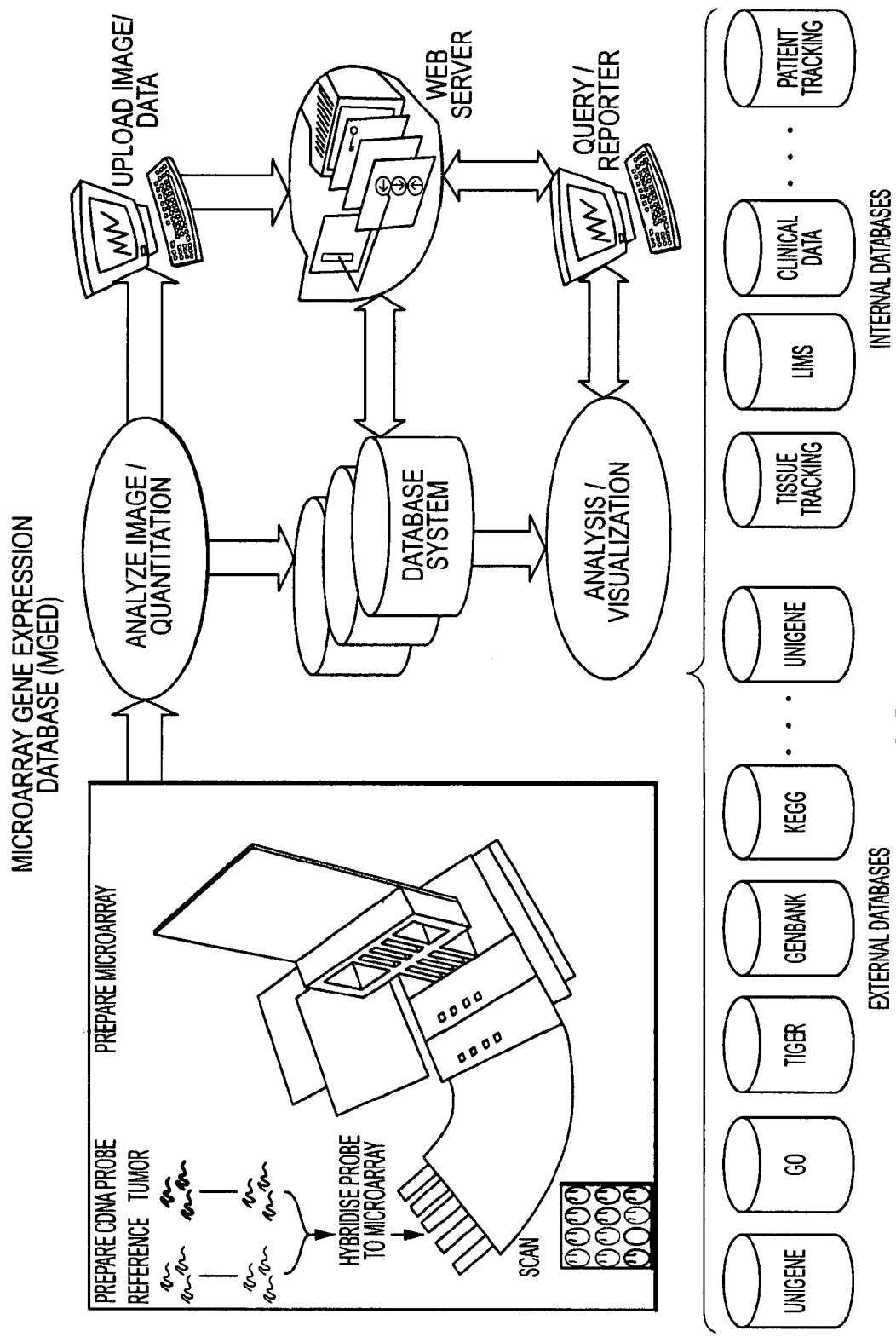
Figure 12:
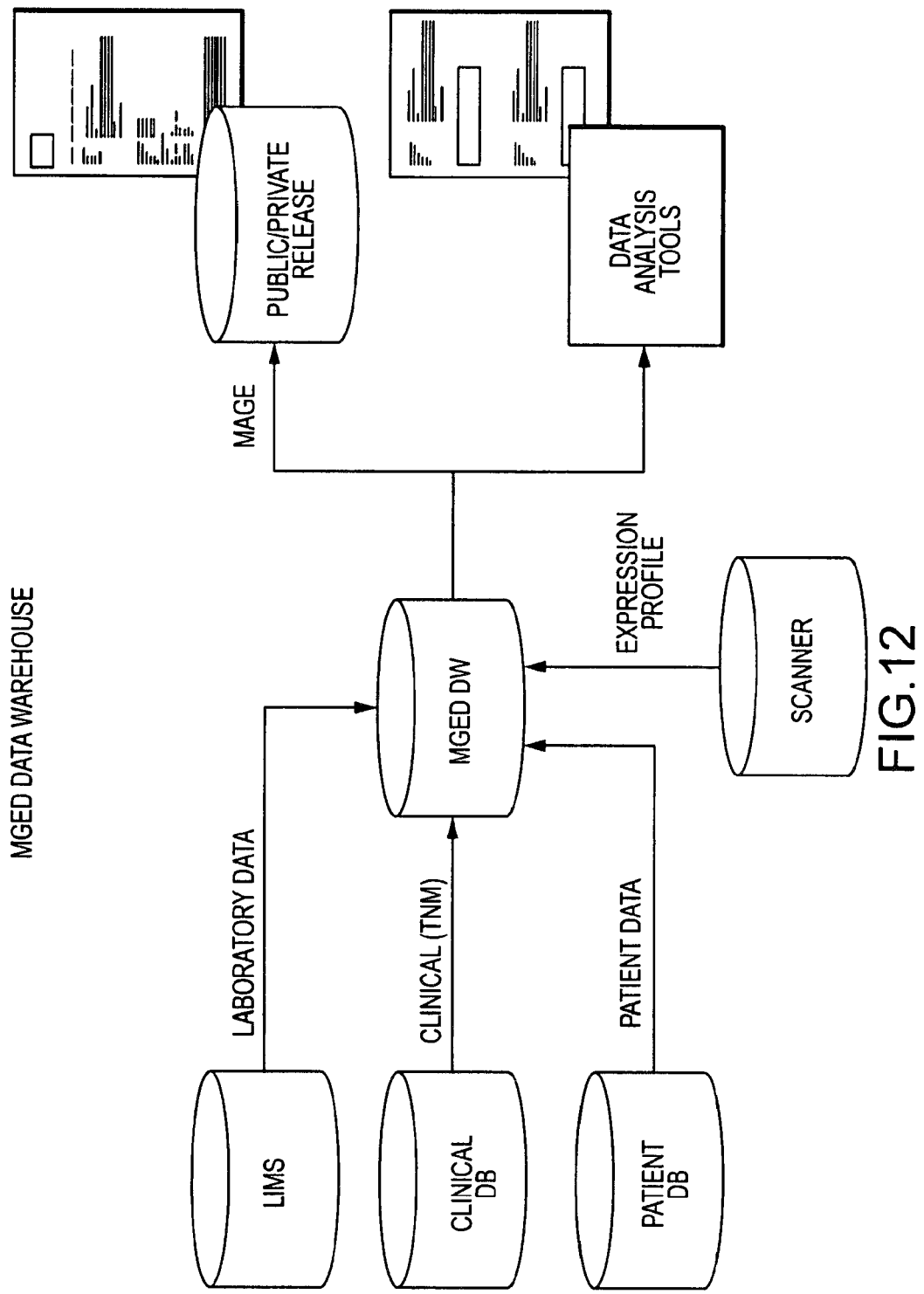

FIG. 11 shows a schematic of an exemplary micro array gene expression database which may be used as part of the information-based personalized medicine drug discovery system and method of the present invention. The micro array gene expression database includes both external databases and internal databases which can be accessed via the web based system. External databases may include, but are not limited to, UniGene, GO, TIGR, GenBank, KEGG. The internal databases may include, but are not limited to, tissue tracking, LIMS, clinical data, and patient tracking. FIG. 12 shows a diagram of an exemplary micro array gene expression database data warehouse which may be used as part of the information-based personalized medicine drug discovery system and method of the present invention. Laboratory data, clinical data, and patient data may all be housed in the micro array gene expression database data warehouse and the data may in turn be accessed by public/private release and utilized by data analysis tools.

Figure 13:
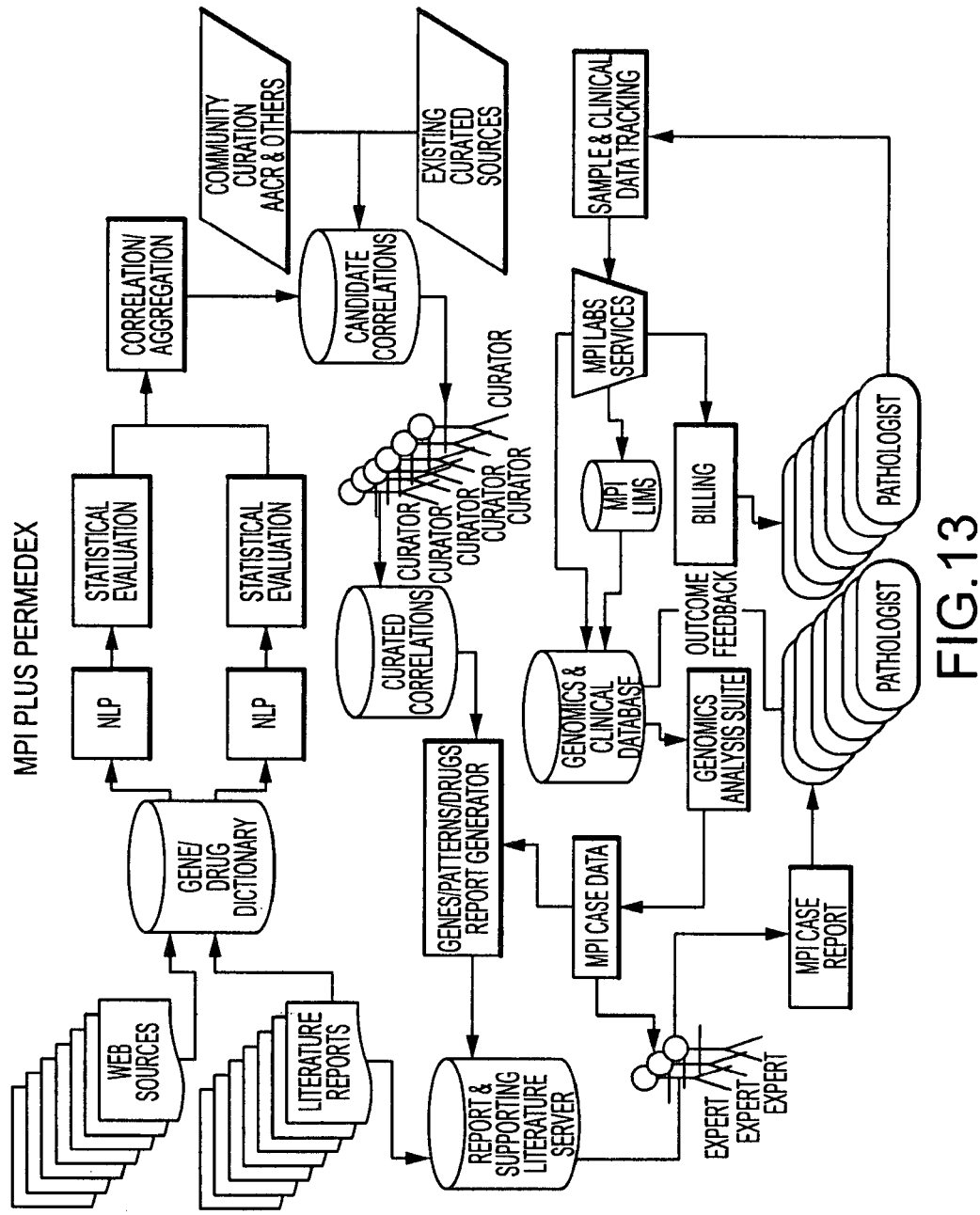
Figure 14:
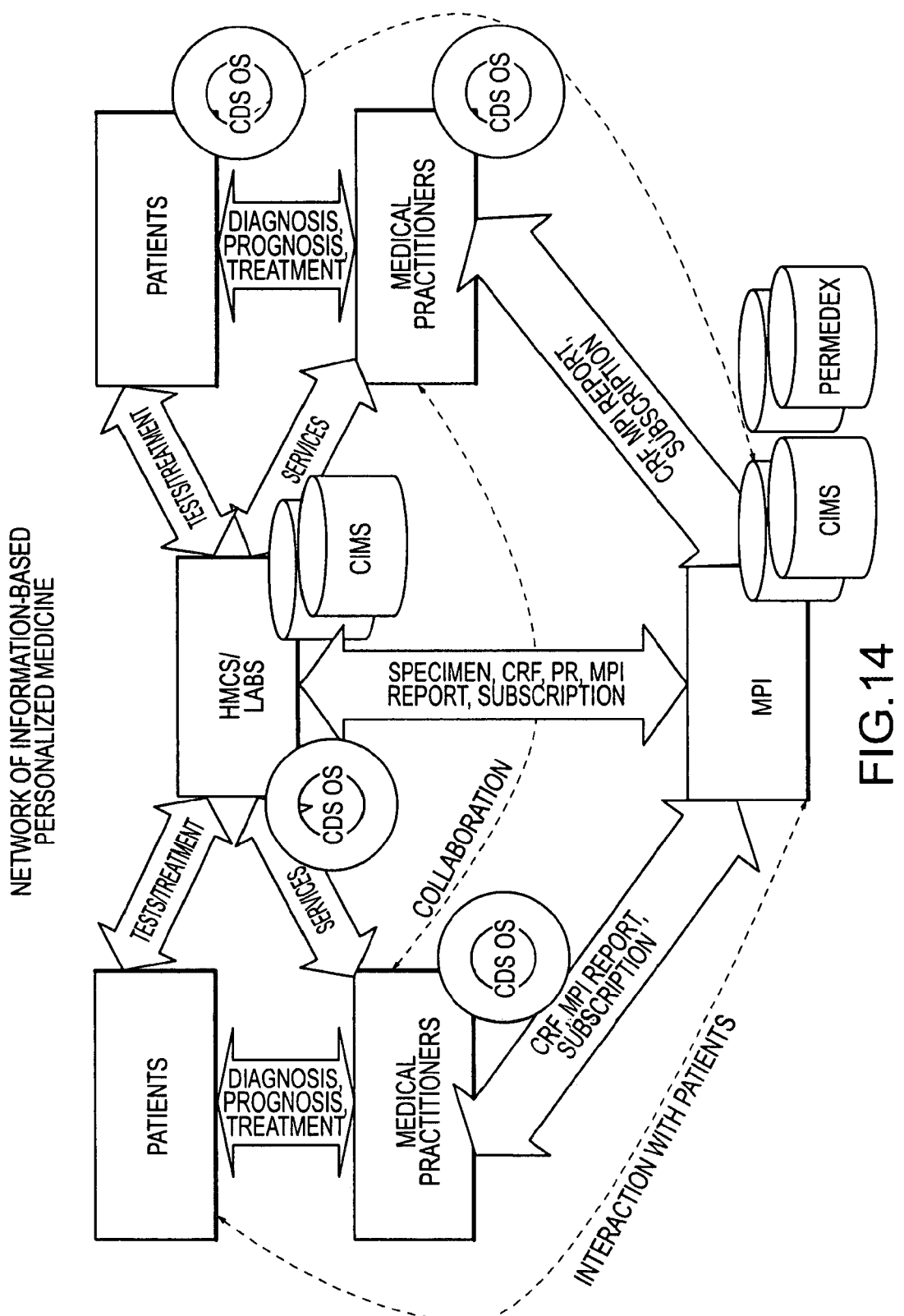

Another schematic showing the flow of information through an information-based personalized medicine drug discovery system and method of the present invention is shown in FIG. 13. Like FIG. 7, the schematic includes clinical information management, medical and literature information management, and financial management of the information-based personalized medicine drug discovery system and method of the present invention. FIG. 14 is a schematic showing an exemplary network of the information-based personalized medicine drug discovery system and method of the present invention. Patients, medical practitioners, host medical centers, and labs all share and exchange a variety of information in order to provide a patient with a proposed therapy or agent based on various identified targets.

Figure 15:
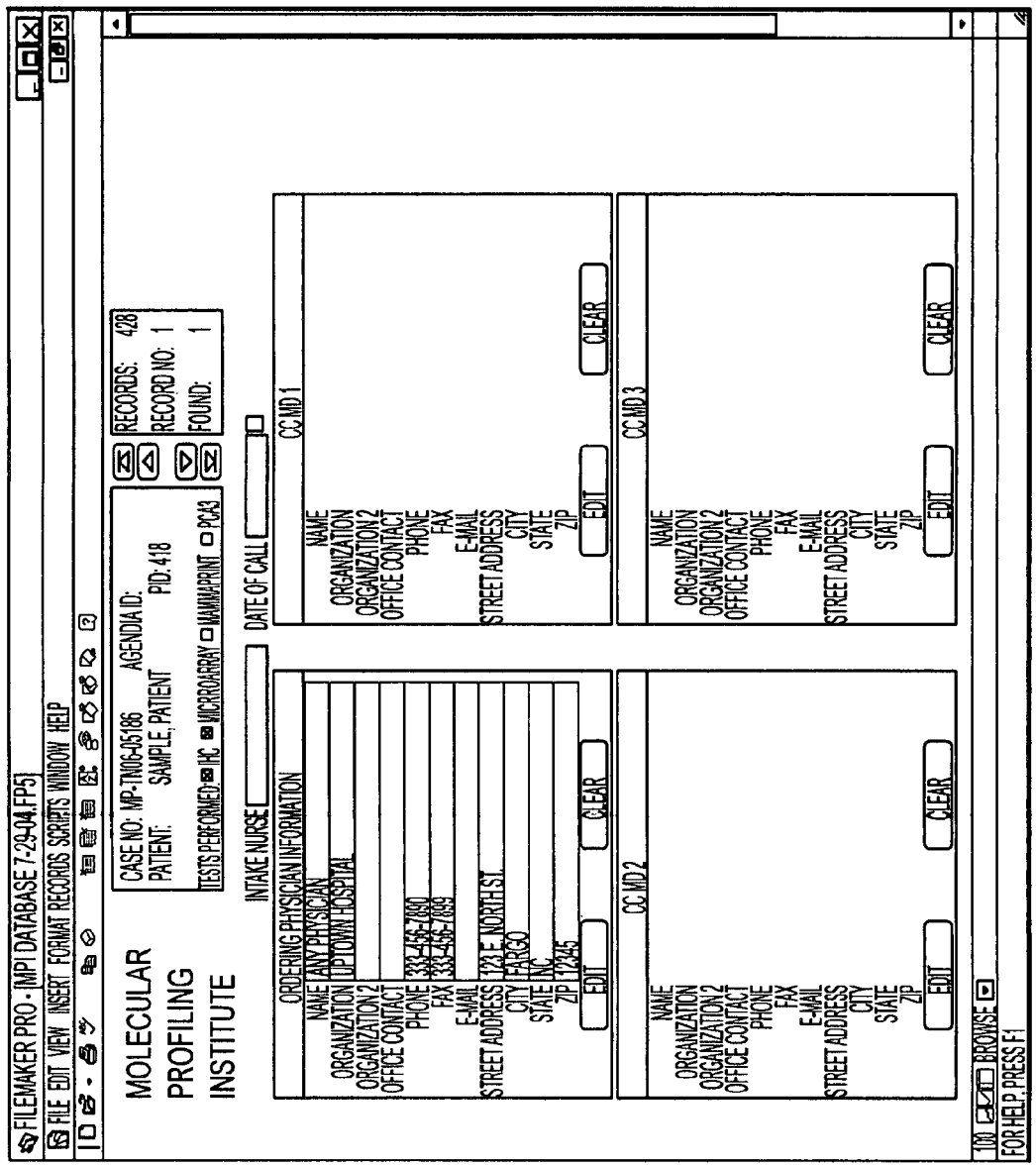
Figure 19:
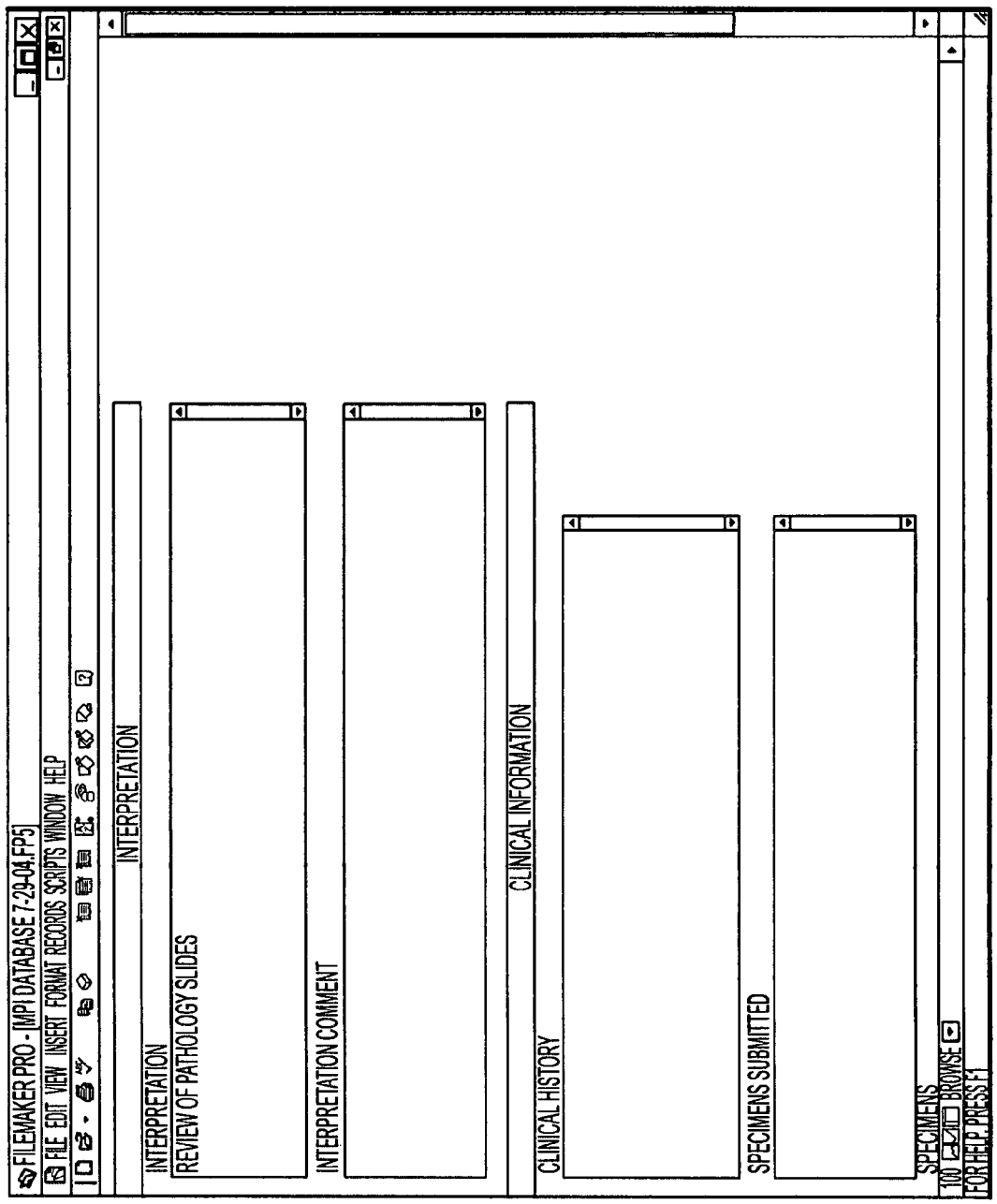

FIGS. 15-25 are computer screen print outs associated with various parts of the information-based personalized medicine drug discovery system and method shown in FIGS. 5-14. FIGS. 15 and 16 show computer screens where physician information and insurance company information is entered on behalf of a client. FIGS. 17-19 show computer screens in which information can be entered for ordering analysis and tests on patient samples.

Figure 20:
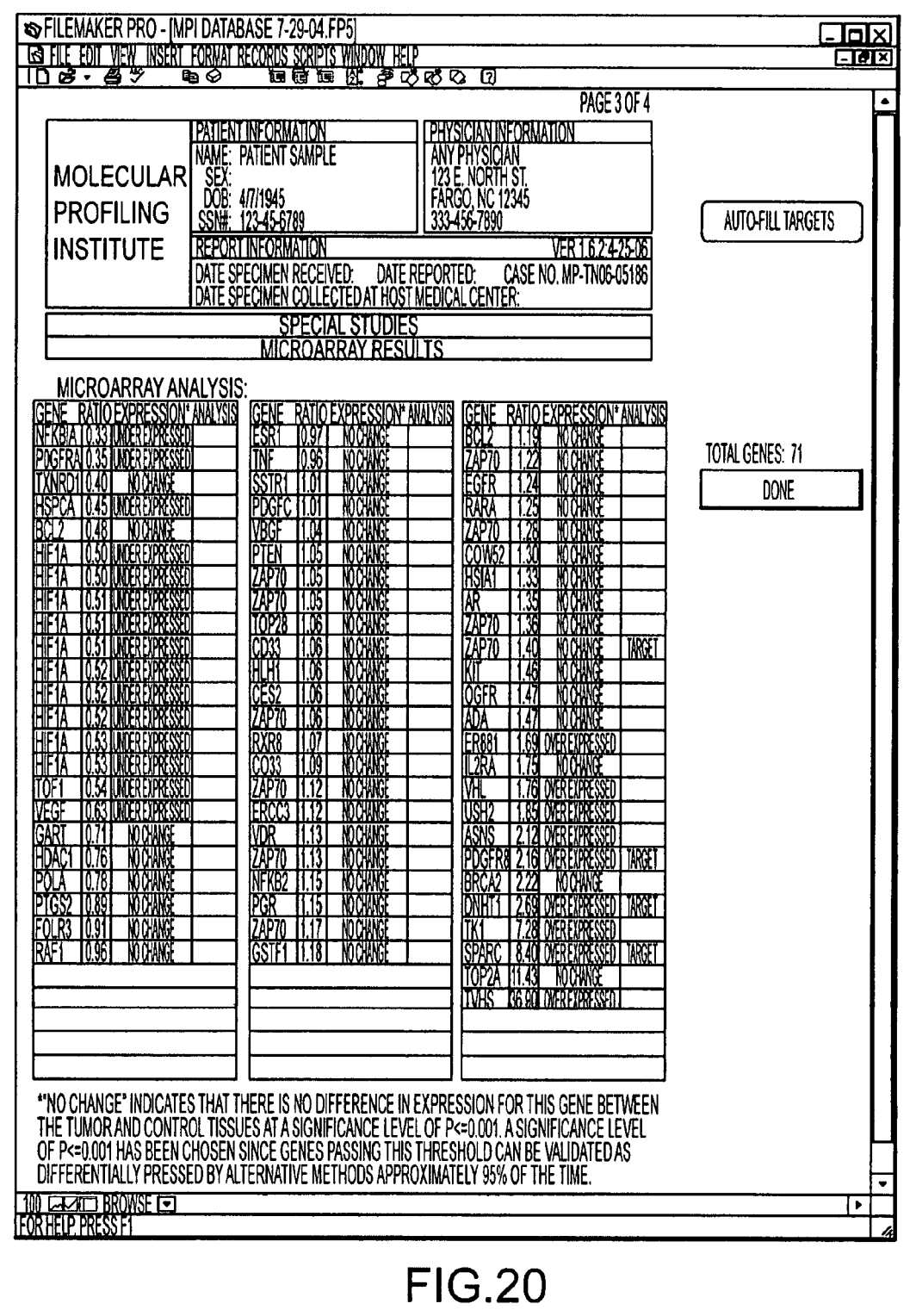
Figure 22:
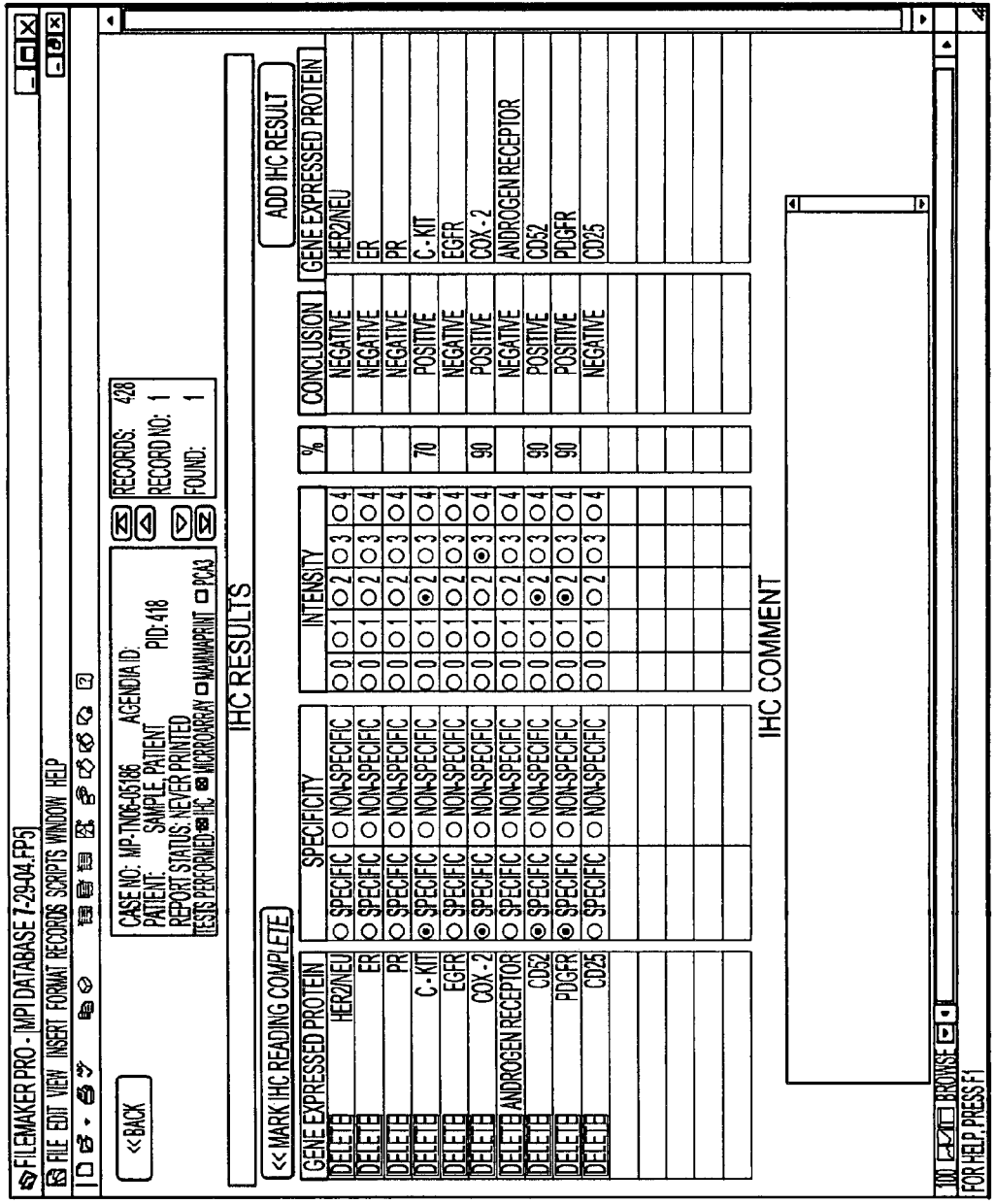

FIG. 20 is a computer screen showing micro array analysis results of specific genes tested with patient samples. This information and computer screen is similar to the information detailed in the patient profile report shown in FIG. 3C. FIG. 22 is a computer screen that shows immunohistochemistry test results for a particular patient for various genes. This information is similar to the information contained in the patient profile report shown in FIG. 3B.

Figure 21:
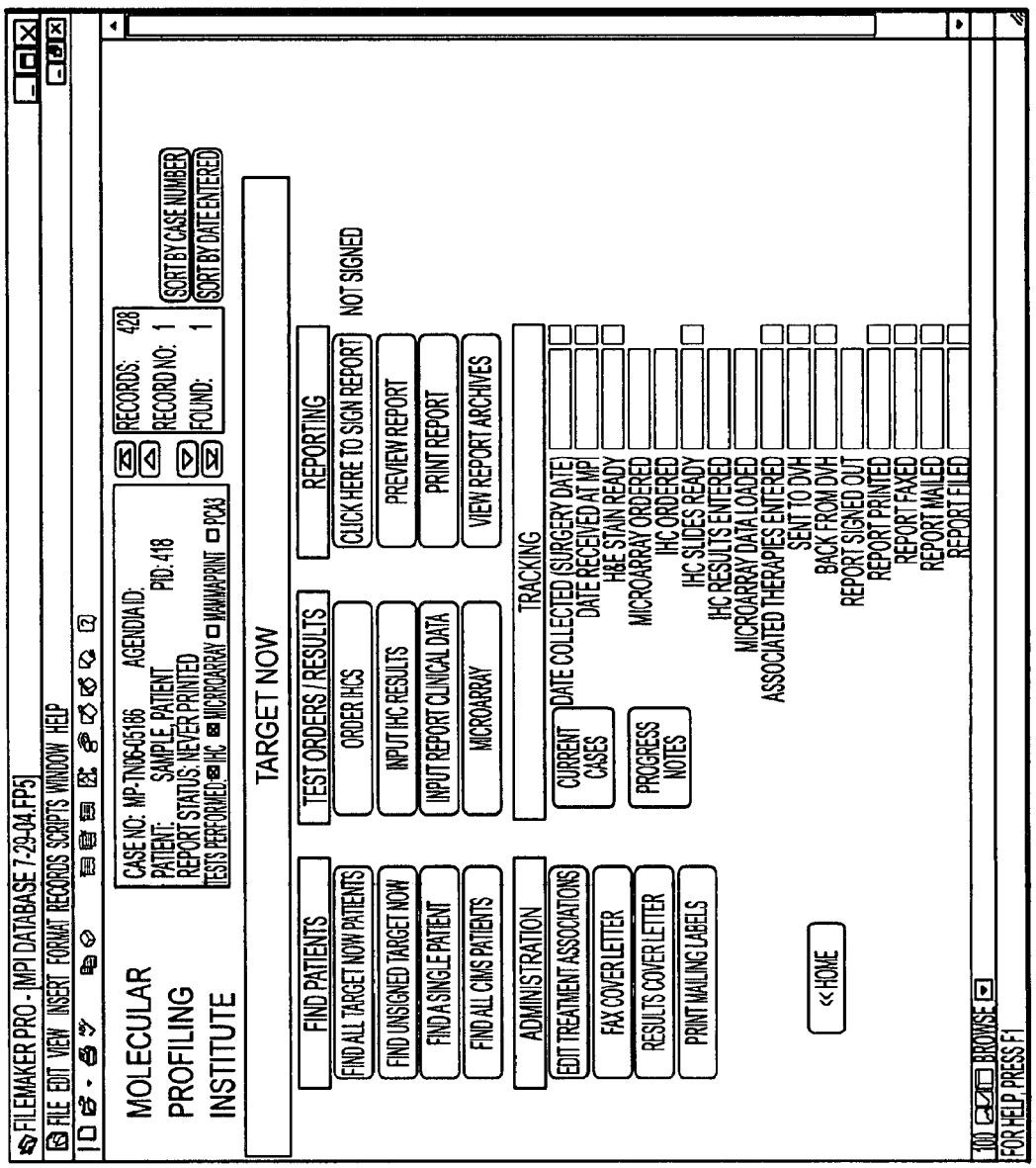

FIG. 21 is a computer screen showing selection options for finding particular patients, ordering tests and/or results, issuing patient reports, and tracking current cases/patients.

Figure 23:
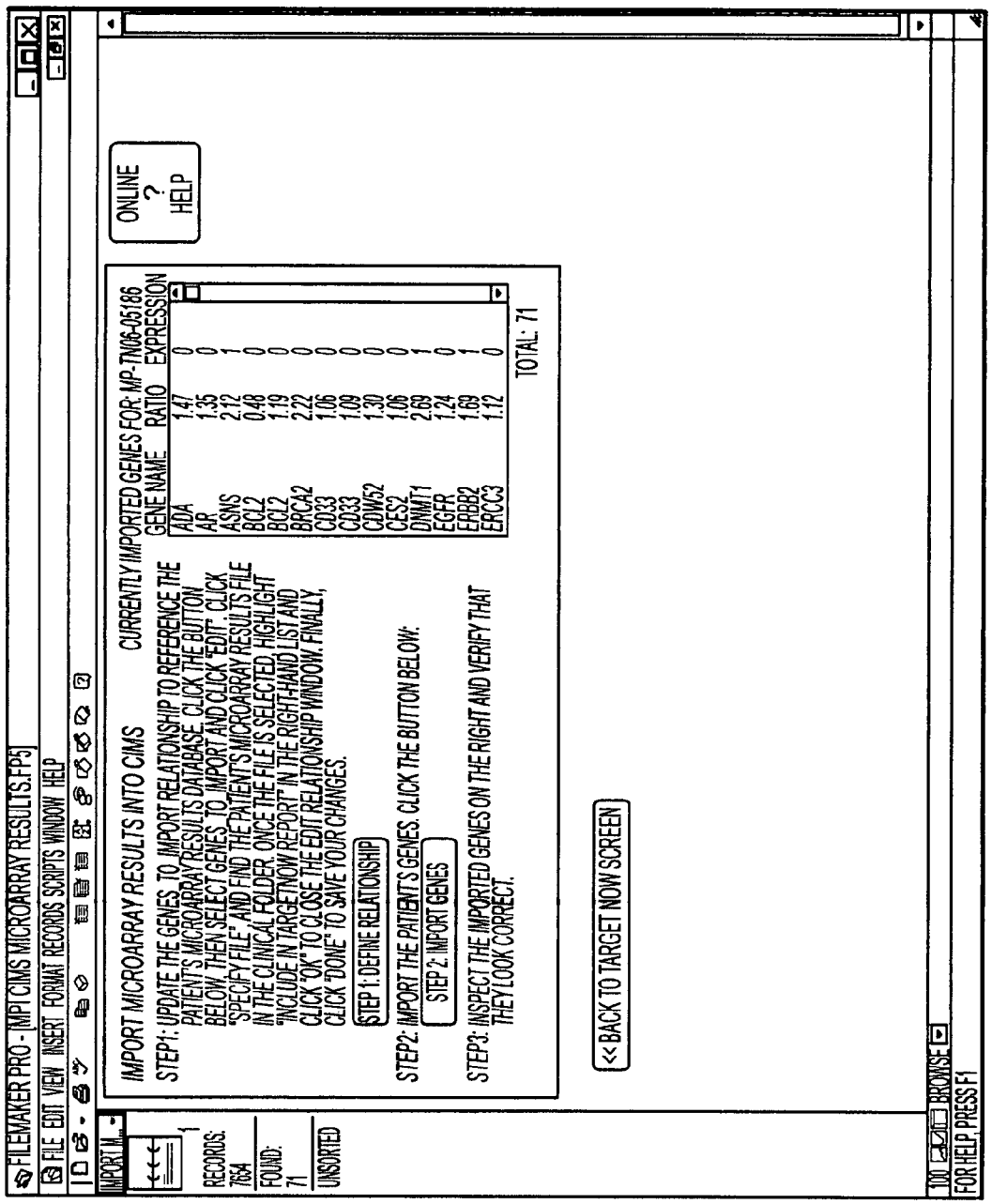
Figure 24:
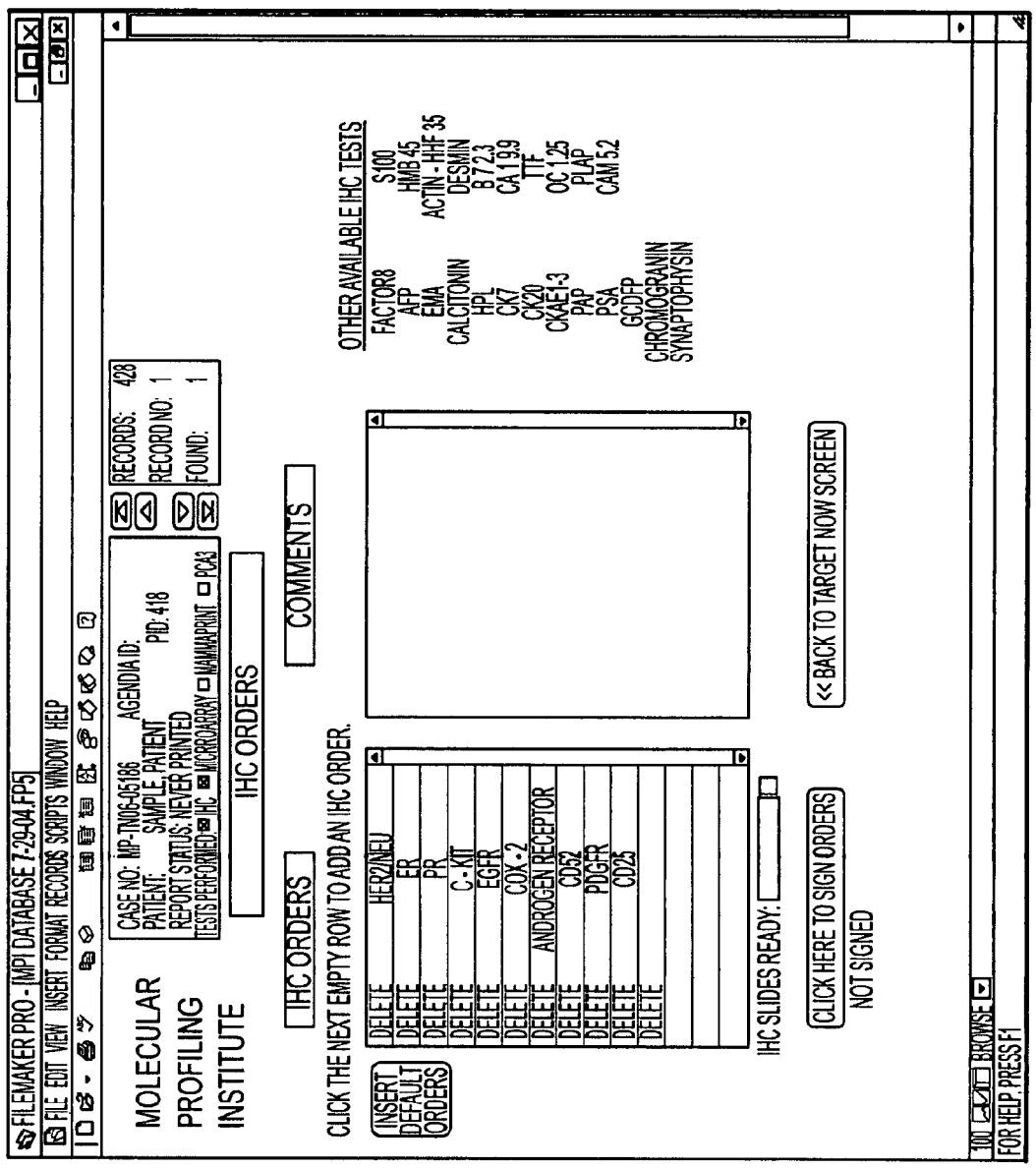
Figure 25:
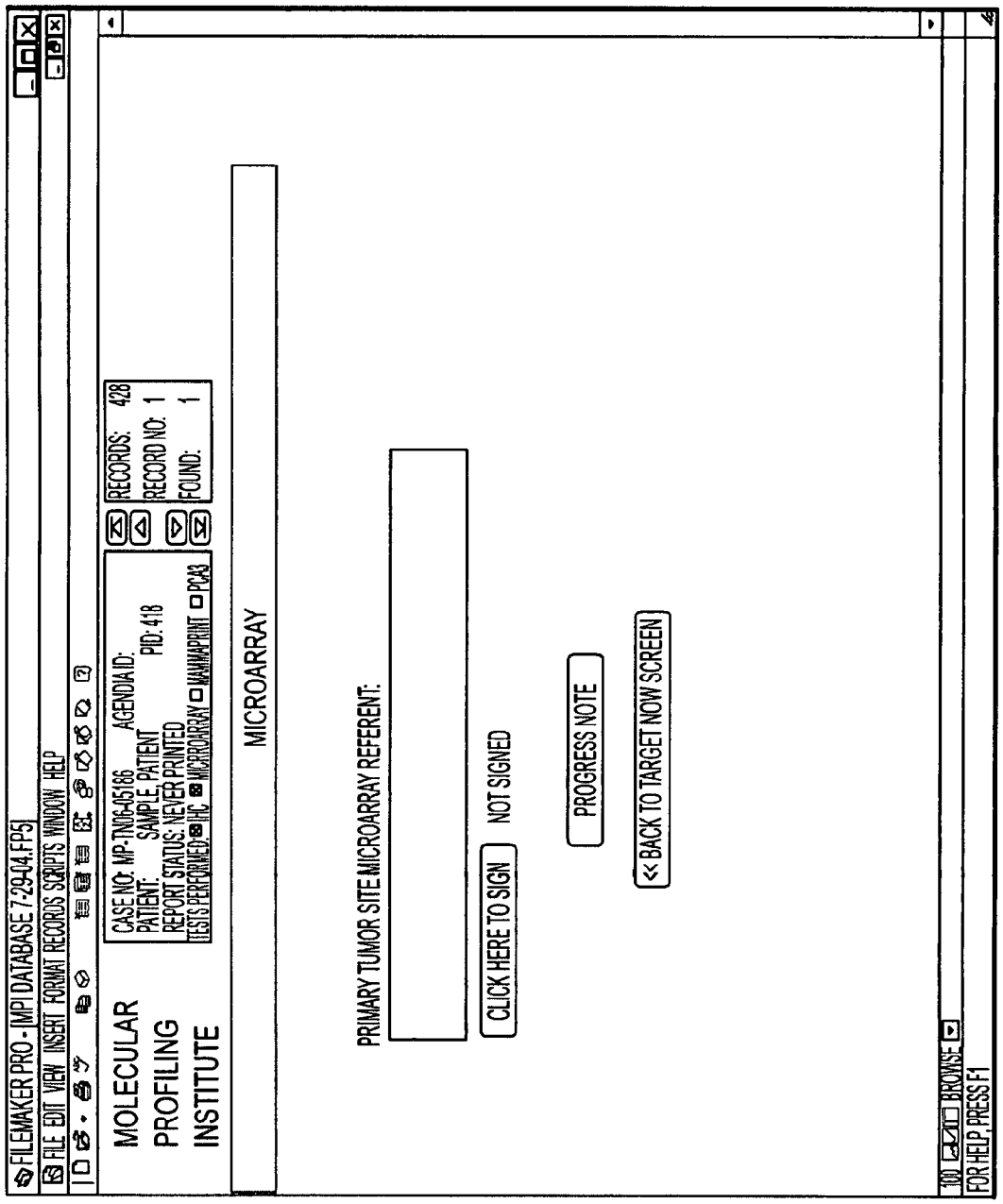

FIG. 23 is a computer screen which outlines some of the steps for creating a patient profile report as shown in FIGS. 3A through 3D. FIG. 24 shows a computer screen for ordering an immunohistochemistry test on a patient sample and FIG. 25 shows a computer screen for entering information regarding a primary tumor site for micro array analysis. It will be understood by those skilled in the art that any number and variety of computer screens may be utilized to enter the information necessary for utilizing the information-based personalized medicine drug discovery system and method of the present invention and to obtain information resulting from utilizing the information-based personalized medicine drug discovery system and method of the present invention.

It will also be understood that the foregoing description is of preferred exemplary embodiments of the invention and that the invention is not limited to the specific forms shown or described herein. Various modifications may be made in the design, arrangement, and type of elements disclosed herein, as well as the steps of utilizing the invention without departing from the scope of the invention as expressed in the appended claims.

What is claimed is:

1. A system for generating a report identifying at least one therapeutic agent for an individual with a cancer comprising:
   a. at least one device configured to assay a plurality of molecular targets in a biological sample to determine molecular profile test values for the plurality of molecular targets, wherein the plurality of molecular targets comprises AR, EGFR, HER2, KIT, MLH1, PTEN, and PDGFRA; and
   b. at least one computer database comprising:
      i. a reference value for each of the plurality of molecular targets; and
      ii. a listing of available therapeutic agents for each of the plurality of molecular targets;
   c. a computer-readable program code comprising instructions to input the molecular profile test values and to compare each of the molecular profile test values with a corresponding reference value from the at least one computer database in (b)(i);
   d. a computer-readable program code comprising instructions to access the at least one computer database and to identify at least one therapeutic agent from the listing of available therapeutic agents for the plurality of molecular targets wherein the comparison to the reference values in (c) indicates a likely benefit of the at least one therapeutic agent; and
   e. a computer-readable program code comprising instructions to generate a report that comprises a listing of the molecular targets for which the comparison to the reference value indicated a likely benefit of the at least one therapeutic agent in (d) and the at least one therapeutic agent identified in (d).

2. The system of claim 1, wherein the molecular profile test values are input into the system from a location that is remote from the at least one computer database.

3. The system of claim 1, wherein the molecular profile test values are input into the system over an internet connection.

4. The system of claim 1, wherein the report is in electronic or paper format.

5. The system of claim 1, wherein the at least one computer database further comprises data corresponding to at least one clinical trial of a member of the plurality of molecular targets.

6. The system of claim 1, wherein the reference value for each of the plurality of molecular targets comprises at least one of a nucleic acid and a protein.

7. The system of claim 1, wherein the molecular profile test values for the plurality of molecular targets are determined after the individual has received drug therapy for the cancer.

8. The system of claim 1, wherein the molecular profile test values are determined by assessing a cell, a tissue sample, a blood sample or a combination thereof.

9. The system of claim 1, wherein the molecular profile test values are determined by performing a test for a gene and/or a protein.

10. The system of claim 1, wherein the reference value for each of the plurality of molecular targets is obtained from at least one individual without the cancer.

11. The system of claim 1, wherein the individual has been treated by and failed to respond to at least one cancer therapeutic.

12. The system of claim 1, wherein the at least one device configured to assay the plurality of molecular targets is configured to perform at least one of immunohistochemistry (IHC), an expression microarray, a comparative genomic hybridization (CGH) microarray, a single nucleotide polymorphism (SNP) microarray, a fluorescent in-situ hybridization (FISH), in-situ hybridization (ISH), and a proteomic array.

13. The system of claim 1, wherein the at least one device configured to assay the plurality of molecular targets is configured to perform at least one of a microarray, genotyping and proteomic analysis.

14. The system of claim 1, wherein the molecular targets assayed in (a) are assayed at the genetic and/or protein level.

* * * * *

(12) INTER PARTES REVIEW CERTIFICATE (2773rd)
United States Patent
Penny et al.

(10) Number: US 9,372,193 K1
(45) Certificate Issued: Aug. 3, 2022

(54) SYSTEM AND METHOD FOR DETERMINING INDIVIDUALIZED MEDICAL INTERVENTION FOR A DISEASE STATE

(71) Applicants: Robert J. Penny; Daniel D. Von Hoff

(72) Inventors: Robert J. Penny; Daniel D. Von Hoff

(73) Assignee: CARIS MPI, INC.

Trial Number:

IPR2019-00170 filed Nov. 5, 2018

Inter Partes Review Certificate for:

Patent No.: 9,372,193
Issued: Jun. 21, 2016
Appl. No.: 14/473,881
Filed: Aug. 29, 2014

The results of IPR2019-00170 are reflected in this inter partes review certificate under 35 U.S.C. 318(b).

INTER PARTES REVIEW CERTIFICATE
U.S. Patent 9,372,193 K1
Trial No. IPR2019-00170
Certificate Issued Aug. 3, 2022

AS A RESULT OF THE INTER PARTES REVIEW PROCEEDING, IT HAS BEEN DETERMINED THAT:

Claims 1-14 are cancelled.

\* \* \* \* \*